United States Patent
Shu et al.

(10) Patent No.: US 12,312,580 B2
(45) Date of Patent: May 27, 2025

(54) STRAIN OF SELENIUM-ENRICHED LACTIPLANTIBACILLUS PLANTARUM KD-2 AND APPLICATIONS IN PREPARING FERMENTED GOAT MILK AND GOAT MILK POWDER

(71) Applicant: Shaanxi Yatai Dairy Co., Ltd., Xianyang (CN)

(72) Inventors: Guowei Shu, Xi'an (CN); Guoliang Li, Xi'an (CN); Hongchang Wan, Xianyang (CN); Xi'e Cheng, Xianyang (CN); Meng Zhang, Xianyang (CN); Jiaxin Li, Xianyang (CN)

(73) Assignee: Shaanxi Yatai Dairy Co., Ltd., Xianyang (CN)

( * ) Notice: Subject to any disclaimer, the term of this patent is extended or adjusted under 35 U.S.C. 154(b) by 0 days.

(21) Appl. No.: 18/738,385

(22) Filed: Jun. 10, 2024

(65) Prior Publication Data

US 2024/0417676 A1    Dec. 19, 2024

(30) Foreign Application Priority Data

Jun. 13, 2023    (CN) .......................... 202310698990.X

(51) Int. Cl.
  *C12N 1/20*    (2006.01)
  *A23C 9/123*    (2006.01)
  *C12R 1/25*    (2006.01)

(52) U.S. Cl.
  CPC ............ *C12N 1/205* (2021.05); *A23C 9/1232* (2013.01); *A23C 9/1234* (2013.01); *C12N 2500/05* (2013.01); *C12R 2001/25* (2021.05)

(58) Field of Classification Search
  CPC .. C12N 1/205; C12N 2500/05; A23C 9/1232; A23C 9/1234; C12R 2001/25
  See application file for complete search history.

(56) References Cited

FOREIGN PATENT DOCUMENTS

| CN | 108504602 A | 9/2018 |
| CN | 110317757 A | 10/2019 |
| CN | 110373347 A | 10/2019 |
| CN | 115769860 A | 3/2023 |
| CN | 115895974 A | 4/2023 |
| KR | 102155849 B1 | 9/2020 |

OTHER PUBLICATIONS

Xu Ying et al., "Study on Enrichment of Selenium by Biotransformation in lactobacillus," Journal of Shaanxi University of Science and Technology, Date of issue: May 28, 2018 Full text Related claims: 1-10.
First Office Action for China Application No. 202310698990.X, mailed Jan. 21, 2024.
Notification to Grant Patent for China Application No. 202310698990.X, mailed Feb. 21, 2024.
First Search Report for China Application No. 202310698990.X, date Jan. 17, 2024.
Supplementary Search Report for China Application No. 202310698990.X, date Jan. 24, 2024.

*Primary Examiner* — Robert A Zeman
(74) *Attorney, Agent, or Firm* — Pilloff Passino & Cosenza LLP; Rachel K. Pilloff; Sean A. Passino

(57) ABSTRACT

A strain of selenium-enriched *Lactiplantibacillus plantarum* KD-2 and applications in fermented goat milk and goat milk powder are provided in the present disclosure. The strain is preserved in China Center for Type Culture Collection on Apr. 13, 2023, with a deposit number of CCTCC NO: M2023478. The *Lactiplantibacillus plantarum* KD-2 is capable of reducing sodium selenite under a condition of buffer solution to prepare nano-selenium, which does not need to be carried out in a culture medium. The *Lactiplantibacillus plantarum* KD-2 is used to prepare selenium-enriched probiotic fermented goat milk, selenium-enriched probiotics and nano-selenium, and the selenium-enriched probiotics and nano-selenium are applied to goat milk powder.

2 Claims, 40 Drawing Sheets

Specification includes a Sequence Listing.

STRAIN OF SELENIUM-ENRICHED *LACTIPLANTIBACILLUS PLANTARUM* KD-2 AND APPLICATIONS IN PREPARING FERMENTED GOAT MILK AND GOAT MILK POWDER

CROSS-REFERENCE TO RELATED APPLICATIONS

This application claims priority to Chinese Patent Application No. 202310698990.X, filed on Jun. 13, 2023, the contents of which are hereby incorporated by reference.

INCORPORATION BY REFERENCE STATEMENT

This statement, made under Rules 77 (b) (5) (ii) and any other applicable rule incorporates into the present specification of an XML file for a "Sequence Listing XML" (see Rule 831 (a)), submitted via the USPTO patent electronic filing system or on one or more read-only optical discs (see Rule 1.52 (e) (8)), identifying the names of each file, the date of creation of each file, and the size of each file in bytes as follows:
File name: sequence.xml
Creation date: 6 Jun. 2024
Byte size: 3191

TECHNICAL FIELD

The present disclosure belongs to the field of microorganisms, and relates to a strain of selenium-enriched *Lactiplantibacillus plantarum* KD-2 and applications in preparing fermented goat milk and goat milk powder.

BACKGROUND

Selenium is an essential trace element for human beings and animals, but it is easy to be taken in excess because of its toxicity. Nano-selenium has the lowest toxicity among all forms of selenium, with higher bioavailability activity in its nano size, so the preparation of nano-selenium is a hot topic of research at present.

Currently, there are chemical and biological methods for the preparation of nano-selenium. Chemical methods have been widely used in the preparation of nano-selenium, and the most common method is to use ascorbic acid to reduce selenium oxide anions such as selenite and selenate, and to make the reduction product obtained by template method and solid-phase method, etc., to be a nanoscale monolithic selenium.

SUMMARY

Biological synthesis of nanoparticles belongs to the category of "green chemistry" compared to chemical methods, which aims to minimize the negative impact of chemical synthesis on the environment. Therefore, the preparation of nanoparticles of various elements from living organisms (microorganisms, plants and animals) and enzymes of such origins is an ecologically harmless alternative to chemical synthesis and is a hot topic of current research. Biological preparation of various nanostructured materials, including selenium nanoparticles produced by microorganisms widely available in nature, has also attracted increasing attention of researchers in the last decade.

Most microbial cells are capable of reducing selenium-oxygen anions ($SeO_4^{2-}$ and $SeO_3^{2-}$) to zero-valent elemental selenium. Anaerobic bacteria such as *Bacillus* sp., *Ralstonia metallidurans* and *Thauera* sp. from contaminated areas together with *Desulfomicrobium* sp. and *Desulfurispirillum indicum* that utilize selenite and selenate are used to reduce selenite and selenonate as electron acceptors in the respiratory chain, which also include a number of inter-root microorganisms (*Rhizobium*, strains of the genus *Pseudomonas*, and *Pseudomonas brasiliensis*). All of these microorganisms are capable of converting toxic selenite or selenate into insoluble zero-valent nanoselenium.

The beneficial health properties of probiotics and the production of beneficial biomolecules through their participation in food fermentation continue to encourage the search for novel probiotics, especially in traditional foods. The most important characteristics of probiotics are acid and bile tolerance, high viability of passing through the intestinal tract, high intestinal adherence and colonization, and long-lasting effects in the host. *Lactobacilli* are the main source of probiotics and have been used in food processes such as production of fermented foods and beverage production. In addition, many reports have also shown that *Lactobacilli* as probiotics have many beneficial effects on humans and animals, such as antibacterial properties, immunomodulation, anti-oncogene, antidiarrheal, antiallergic and antioxidant activities. Similar to the ability of many microorganisms to absorb and transform selenium ions, under appropriate conditions, some *Lactobacilli* may accumulate a large number of trace elements, such as selenium, zinc and copper, and incorporate them into organic compounds. *Lactobacillus* strains have been used to bio-enrich and bio-transform inorganic selenium into organic and nano-selenium, and the beneficial effects of these strains on health have been demonstrated in a number of in vitro and in vivo studies. At present, an international operation is to convert selenium salts into nano-selenium by adding inorganic selenium salts into the medium for lactic acid bacteria growth, but there are problems such as the complexity of the fermentation broth composition affecting the subsequent isolation and purification of the nano-selenium.

In order to solve the problems in the prior art, the present disclosure provides a selenium-enriched *Lactiplantibacillus plantarum* KD-2 and applications in fermented goat milk and goat milk powder. The *Lactiplantibacillus plantarum* KD-2 reduces sodium selenite to prepare nano-selenium under a condition of buffer solution, which may not need to be carried out in culture medium; the *Lactiplantibacillus plantarum* KD-2 is used to prepare selenium-enriched probiotic fermented goat milk, selenium-enriched probiotics and nano-selenium, and the selenium-enriched probiotics are applied in goat milk powder.

The present disclosure is realized by following technical schemes.

A strain of *Lactiplantibacillus plantarum* KD-2, deposited in China Center for Type Culture Collection on Apr. 13, 2023, with a deposit number of CCTCC NO: M2023478.

A preparation method of the selenium-enriched *Lactiplantibacillus plantarum* KD-2, including inoculating *Lactiplantibacillus plantarum* KD-2 strain into a culture medium, performing activation culture, inoculating into an MRS broth culture medium after the activation culture, placing in an incubator for culture, centrifuging after the *Lactiplantibacillus plantarum* KD-2 strain grows to a logarithmic phase, taking a bacterial sludge and adding phosphate buffer, then adding sodium selenite solution to obtain a bacterial suspension, followed by placing in an incubator for transformation to obtain a transformation solution; centrifuging the transformation solution, collecting a precipitate, washing with normal saline, and centrifuging again to obtain selenium-enriched *Lactiplantibacillus plantarum* KD-2; where the *Lactiplantibacillus plantarum* KD-2 strain is the *Lactiplantibacillus plantarum* KD-2 strain described above.

Optionally, a concentration of sodium selenite in the bacterial suspension is 100-200 microgram per milliliter (μg/mL), a concentration of the *Lactiplantibacillus plantarum* KD-2 is 0.033-0.067 mg/mL, and a pH of the bacterial suspension is 6.66-7.34.

Optionally, a temperature of the transformation is 35-39 degrees Celsius (C) and a duration of the transformation is 44 hours (h)-51 h.

A strain of selenium-enriched *Lactiplantibacillus plantarum* KD-2 obtained by the preparation method.

A probiotic goat milk powder, including goat milk powder and the selenium-enriched *Lactiplantibacillus plantarum* KD-2.

A method for preparing nano-selenium by transforming sodium selenite with *Lactiplantibacillus plantarum* KD-2 strain, including extracting nano-selenium from the transformation solution; where the transformation solution is prepared by the preparation method.

Optionally, extracting nano-selenium from the transformation solution specifically includes: centrifuging the transformation solution and collecting a precipitate to obtain nano-selenium-enriched *Lactiplantibacillus plantarum* KD-2; adding the nano-selenium-enriched *Lactiplantibacillus plantarum* KD-2 into phosphate buffer, adding lysozyme, standing for enzymolysis, then ultrasonically crushing, adding sterile water and 1-octanol to a washed precipitate, resuspending, centrifuging, standing, and collecting a precipitate, washing, and freeze-drying to obtain the nano-selenium.

A method for preparing a selenium-enriched *Lactiplantibacillus plantarum* fermented goat milk, including: adding water to goat milk powder, sterilizing, adding a leavening agent, *Lactiplantibacillus plantarum* KD-2 strain and sodium selenite, and fermenting to obtain the selenium-enriched *Lactiplantibacillus plantarum* fermented goat milk; where the *Lactiplantibacillus plantarum* strain is the *Lactiplantibacillus plantarum* KD-2 strain.

A selenium-enriched *Lactiplantibacillus plantarum* fermented goat milk obtained by the preparation method.

Compared with the prior art, the present disclosure has the following beneficial effects.

*Lactiplantibacillus plantarum* KD-2 transforms sodium selenite by bacterial cells to prepare nano-selenium, without need to be carried out in a culture medium, and the transformation solution has simple components and strong selenium-enriched ability per cell, thus obtaining the selenium-enriched *Lactiplantibacillus plantarum*; the selenium nanopowder of *Lactiplantibacillus plantarum* is prepared by freeze-drying after centrifugation and addition of a protective agent; the selenium-enriched *Lactiplantibacillus plantarum* slurry obtained by centrifugation is subjected to enzymolysis, wall-breaking and separation to obtain the nano-selenium. The *Lactiplantibacillus plantarum* KD-2 of the present disclosure may be used for preparing selenium-enriched fermented goat milk, which serves to accelerate fermentation and shorten fermentation time; with *Lactiplantibacillus plantarum* KD-2 and nano-selenium, the texture characteristics of fermented goat milk are obviously improved; the *Lactiplantibacillus plantarum* nano-selenium powder and nano-selenium may also be added into goat milk powder, so that the oxidation resistance of goat milk powder is improved and the goat milk powder remains stable during storage.

DETAILED DESCRIPTION OF THE EMBODIMENTS

In order to further understand the present disclosure, the following description is made with embodiments, which are only for further explaining the features and advantages of the present disclosure, and are not used to limit the claims of the present disclosure.

Embodiment 1 Isolation and Identification of *Lactiplantibacillus plantarum* KD-2 of the Present Disclosure 1. Isolation of *Lactiplantibacillus plantarum* KD-2

Commercially available kefir grains are inoculated at 5% into sterilized and cooled goat milk, and then fermented at room temperature for 24 h as a sample, from which 60 strains of selenium-enriched *Lactobacilli* are screened by the plate separation method (with the addition of sodium selenite in the plate), and then a *Lactobacillus* with strong capacity of nano-selenium producing is obtained by repeatedly initial screening and re-screening.

2. Identification of *Lactiplantibacillus plantarum* KD-2

The strain is identified by 16S rDNA. After amplifying and purifying the target fragment, the strain is characterized according to the homology analysis of some gene fragments of 16S rDNA, and the measured sequence is compared and analyzed with the base sequence in NCBI database to construct the phylogenetic tree of the strain, as shown in FIG. 1, with the base pair sequence as follows (SEQ ID NO.1):

```
GGGCGGTGTGTACAAGGCCCGGGAACGTATTCACCGCGGCATGCTG
ATCCGCGATTACTAGCGATTCCGACTTCATGTAGGCGAGTTGCAG
CCTACAATCCGAACTGAGAATGGCTTTAAGAGATTAGCTTACTCT
CGCGAGTTCGCAACTCGTTGTACCATCCATTGTAGCACGTGTGTA
GCCCAGGTCATAAGGGGCATGATGATTTGACGTCATCCCCACCTT
CCTCCGGTTTGTCACCGGCAGTCTCACCAGAGTGCCCAACTTAAT
GCTGGCAACTGATAATAAGGGTTGCGCTCGTTGCGGGACTTAACC
CAACATCTCACGACACGAGCTGACGACAACCATGCACCACCTGTA
TCCATGTCCCCGAAGGGAACGTCTAATCTCTTAGATTTGCATAGT
ATGTCAAGACCTGGTAAGGTTCTTCGCGTAGCTTCGAATTAAACC
ACATGCTCCACCGCTTGTGCGGGCCCCCGTCAATTCCTTTGAGTT
TCAGCCTTGCGGCCGTACTCCCCAGGCGGAATGCTTAATGCGTTA
GCTGCAGCACTGAAGGGCGGAAACCCTCCAACACTTAGCATTCAT
CGTTTACGGTATGGACTACCAGGGTATCTAATCCTGTTTGCTACC
CATACTTTCGAGCCTCAGCGTCAGTTACAGACCAGACAGCCGCCT
TCGCCACTGGTGTTCTTCCATATATCTACGCATTTCACCGCTACA
CATGGAGTTCCACTGTCCTCTTCTGCACTCAAGTTTCCCAGTTTC
CGATGCACTTCTTCGGTTGAGCCGAAGGCTTTCACATCAGACTTA
AAAAACCGCCTGCGCTCGCTTTACGCCCAATAAATCCGGACAACG
CTTGCCACCTACGTATTACCGCGGCTGCTGGCACGTAGTTAGCCG
TGGCTTTCTGGTTAAATACCGTCAATACCTGAACAGTTACTCTCA
GATATGTTCTTCTTTAACAACAGAGTTTTACGAGCCGAAACCCTT
CTTCACTCACGCGGCGTTGCTCCATCAGACTTTCGTCCATTGTGG
AAGATTCCCTACTGCTGCCTCCCGTAGGAGTTTGGGCCGTGTCTC
AGTCCCAATGTGGCCGATTACCCTCTCAGGTCGGCTACGTATCAT
TGCCATGGTGAGCCGTTACCCCACCATCTAGCTAATACGCCGCGG
GACCATCCAAAAGTGATAGCCGAAGCCATCTTTCAAGCTCGGACC
ATGCGGTCCAAGTTGTTATGCGGTATTAGCATCTGTTTCCAGGTG
TTATCCCCCGCTTCTGGGCAGGTTTCCCACGTGTTACTCACCAGT
TCGCCACTCAC.
```

Figure 1:
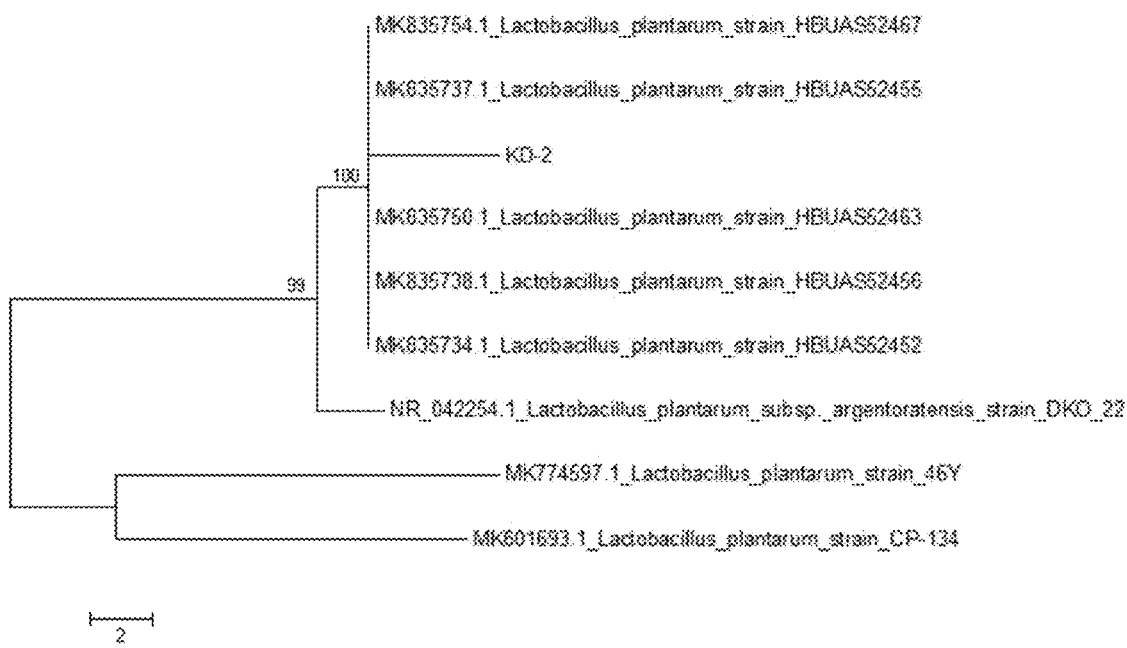
FIG. 1 is a phylogenetic tree of *Lactiplantibacillus plantarum* KD-2.

As may be seen from FIG. 1, the homology between the strain and *Lactiplantibacillus plantarum* strain HBUAS52455 reaches 100%, indicating that the strain is a strain of *Lactiplantibacillus plantarum*, an is named as *Lactiplantibacillus plantarum* KD-2; the *Lactiplantibacillus plantarum* KD-2 is deposited in China Center for Type Culture Collection on Apr. 13, 2023, at Wuhan University, No. 299 Bayi Road, Wuchang District, Wuhan City, Hubei Province, with a deposit number of CCTCC NO: M2023478.

Embodiment 2 Preparation of Selenium-Enriched *Lactiplantibacillus plantarum* KD-2

*Lactiplantibacillus plantarum* KD-2 is activated and cultured in MRS broth medium. After three generations of continuous activation, it is inoculated in MRS broth medium with an inoculation amount of 5% (v/v) and cultured in an incubator at 37° C. for 24 h. After the growth of *Lactiplantibacillus plantarum* KD-2 reaches the logarithmic phase, a certain amount of bacterial suspension is taken for centrifugal separation to obtain cells, and phosphate buffer (pH=6.4) is used for washing; after washing, phosphate buffer is added to the precipitate to obtain bacterial suspension, and sodium selenite solution is added to the bacterial suspension to make its final concentration 100 μg/mL, and then it is placed in an incubator at 37° C. for 24 h.

The color of the obtained culture medium is red, which indicates that nano elemental selenium is produced in the culture medium, that is, *Lactiplantibacillus plantarum* KD-2 is capable of transforming sodium selenite into nano-selenium by using bacterial cells without culture medium. The sodium selenite transformation rate of the strain is 86.23%, and the content of nano-selenium per unit cell is 1.13 mg/g.

Embodiment 3 Optimization of Preparation of Nano-Selenium by *Lactiplantibacillus plantarum* KD-2

1. Effect of Duration on Preparation of Nano-Selenium by *Lactiplantibacillus plantarum* KD-2

*Lactiplantibacillus plantarum* KD-2 is cultured in MRS broth for 24 h, centrifuged, and the obtained bacterial sludge is washed, and then phosphate buffer and sodium selenite solution are added to obtain a bacterial suspension, with the bacterial sludge concentration of 0.05 g/mL and the pH of 6.4, and the sodium selenite concentration of 100 μg/mL. The bacterial suspension is transformed at 37° C. at constant temperature for different duration (12, 24, 36, 48 and 60 h), the sodium selenite reduction rate and the a* red value of the culture solution are determined and the results are shown in FIG. 2.

Figure 2:
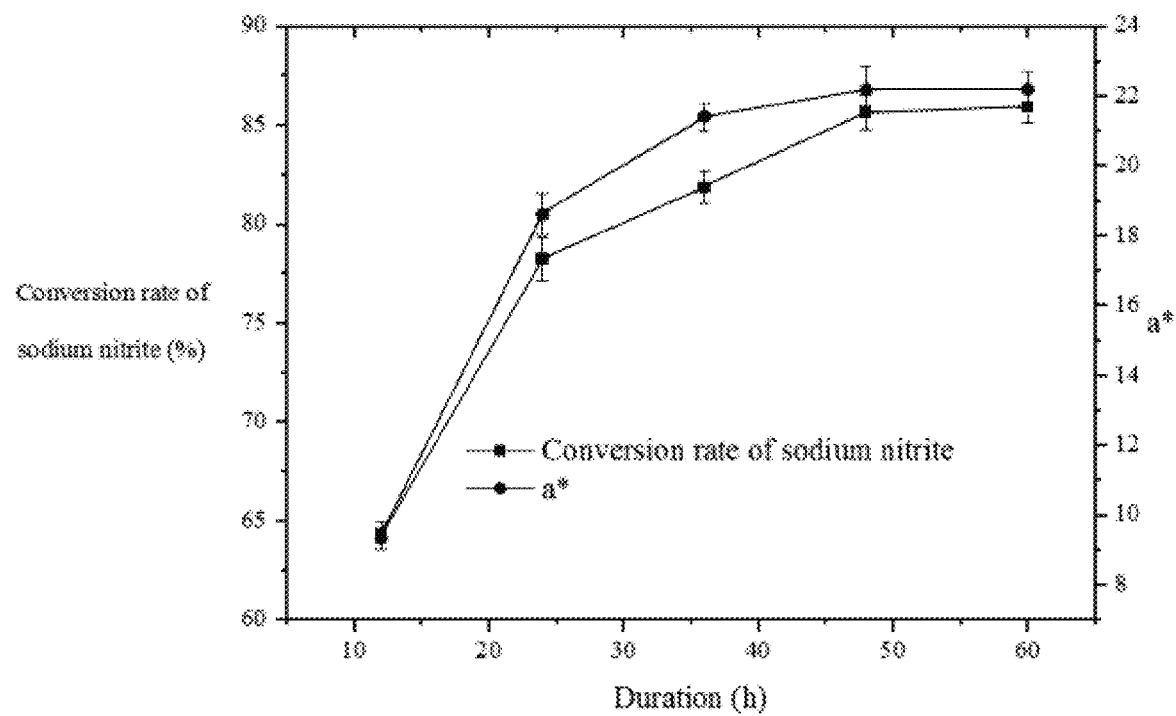
FIG. 2 shows the influence of different duration on the preparation of selenium-enriched *Lactiplantibacillus plantarum* KD-2.

It is observed from FIG. 2 that the conversion rate of sodium selenite gradually increases with the increase of time, and after reaching 85.83% after 48 hours, the conversion rate of sodium selenite gradually changes smoothly with the increase of time. This is because the reductase in bacteria gradually reduces selenite to nano-selenium, and with the increase of time, the activity of bacteria gradually decreases, resulting in the maximum effect of reductase, so the conversion rate of sodium selenite is basically unchanged after 48 h. The a* red value of bacterial suspension is basically consistent with the conversion rate of sodium selenite, and it changes slowly after reaching 22.16 in 48 h.

2. Effect of Temperature on Preparation of Nano-Selenium by *Lactiplantibacillus plantarum* KD-2

Figure 4:
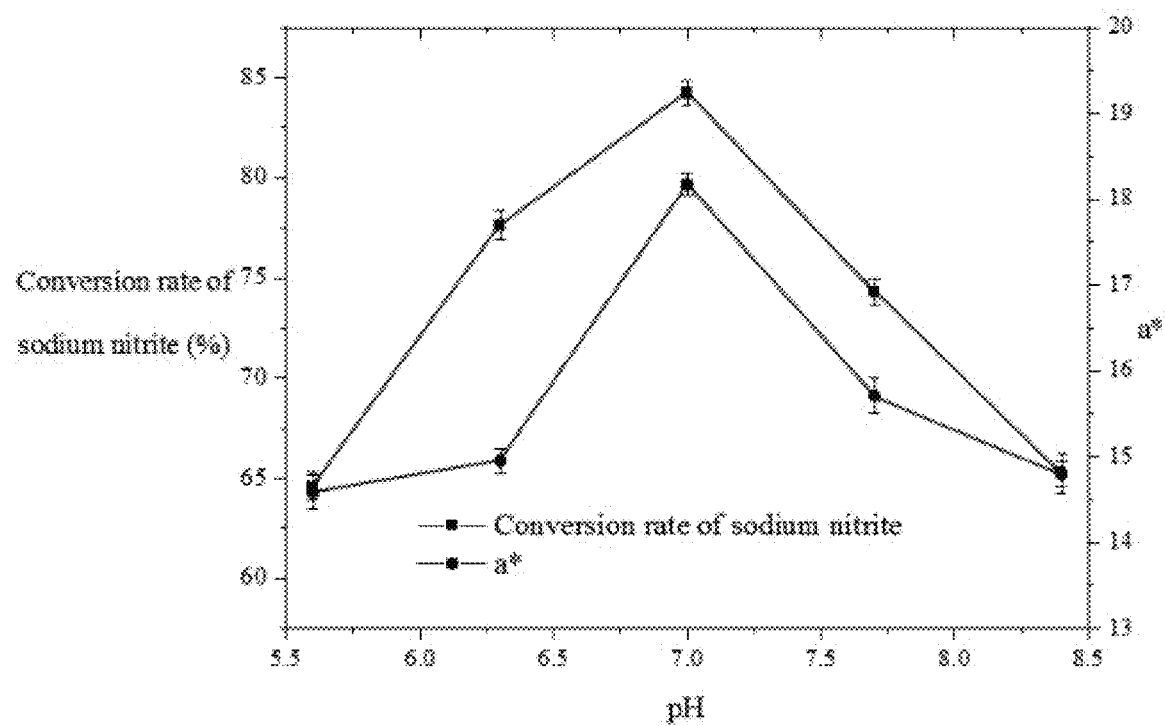
FIG. 4 shows the effects of different pH values during the preparation of selenium-enriched *Lactiplantibacillus plantarum* KD-2.

The transformation temperature is adjusted to 33° C., 35° C., 37° C., 39° C. and 41° C. respectively, and the transformation duration is 48 h. The influence of temperature on the preparation of nano-selenium by *Lactiplantibacillus plantarum* KD-2 is analyzed, and the results are shown in FIG. 4.

Figure 3:
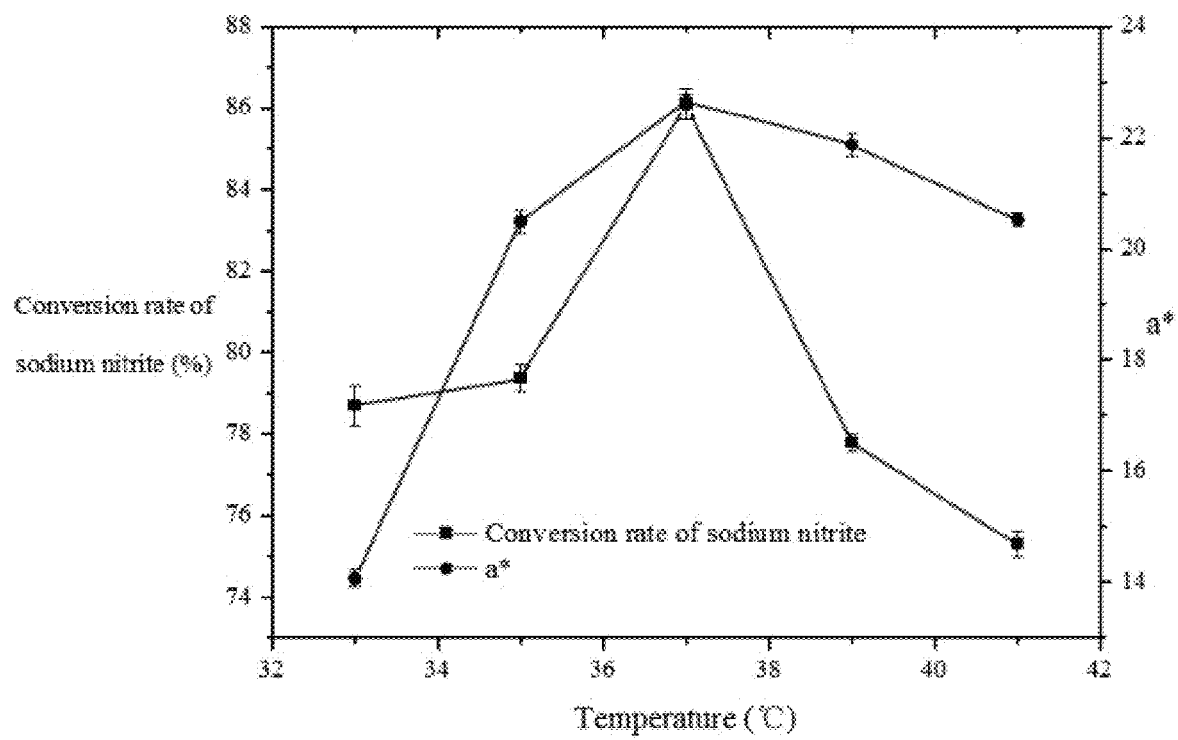
FIG. 3 shows the effects of different temperatures during the preparation of selenium-enriched *Lactiplantibacillus plantarum* KD-2.

As can be seen from FIG. 3, the conversion rate of sodium selenite first increases and then decreases with the increase of temperature, and when the temperature reaches 37° C., the conversion rate of sodium selenite reaches the maximum of 86.10%. This is because with the increase of temperature, the reductase in the bacteria gradually reaches the optimum temperature, which leads to the maximum reducing ability of sodium selenite. When the temperature is too high, the activity of the bacteria decreases, so the conversion rate of selenite decreases. The change of a* red value of bacterial suspension is consistent with the change of sodium selenite conversion rate. When the temperature is 37° C., the a* red value reaches the maximum of 22.64, indicating that the range of 35-39° C. is the suitable temperature for the transformation of *Lactiplantibacillus plantarum* KD-2 to prepare nano-selenium.

3. Effect of pH on Preparation of Nano-Selenium by *Lactiplantibacillus plantarum* KD-2

The bacterial suspension is adjusted to pH values of 5.6, 6.3, 7, 7.7 and 8.4, respectively, and transformed at a constant temperature of 37° C. for 48 h. The effect of pH on the preparation of selenium nanoparticles is analyzed, and the results are shown in FIG. 4.

It is observed from FIG. 4 that the conversion rate of sodium selenite first increases and then decreases with the increase of pH value.

When the pH value reaches 7, the conversion rate of sodium selenite reaches 54.13% at the maximum. When the pH values are weakly acidic 5.6 and weakly alkaline 8.4 respectively, the conversion rates of sodium selenite are relatively low, being 64.59% and 60.24% respectively, indicating that *Lactiplantibacillus plantarum* KD-2 is more suitable for reducing sodium selenite under neutral conditions. The change of a* red value also reaches the maximum of 18.17 at pH 7. Therefore, the pH value of 7.0 is selected to further optimize the conversion process parameters.

4. Effect of Sodium Selenite Concentration on the Preparation of Nano-Selenium by *Lactiplantibacillus plantarum* KD-2

The bacterial suspension is adjusted to have the concentration of sodium selenite at 50, 100, 150, 200 and 250 μg/mL respectively, and then transformed at a constant temperature of 37° C. for 48 h. The effect of the concentration of sodium selenite on the preparation of nano-selenium is analyzed, and the results are shown in FIG. 5.

Figure 5:
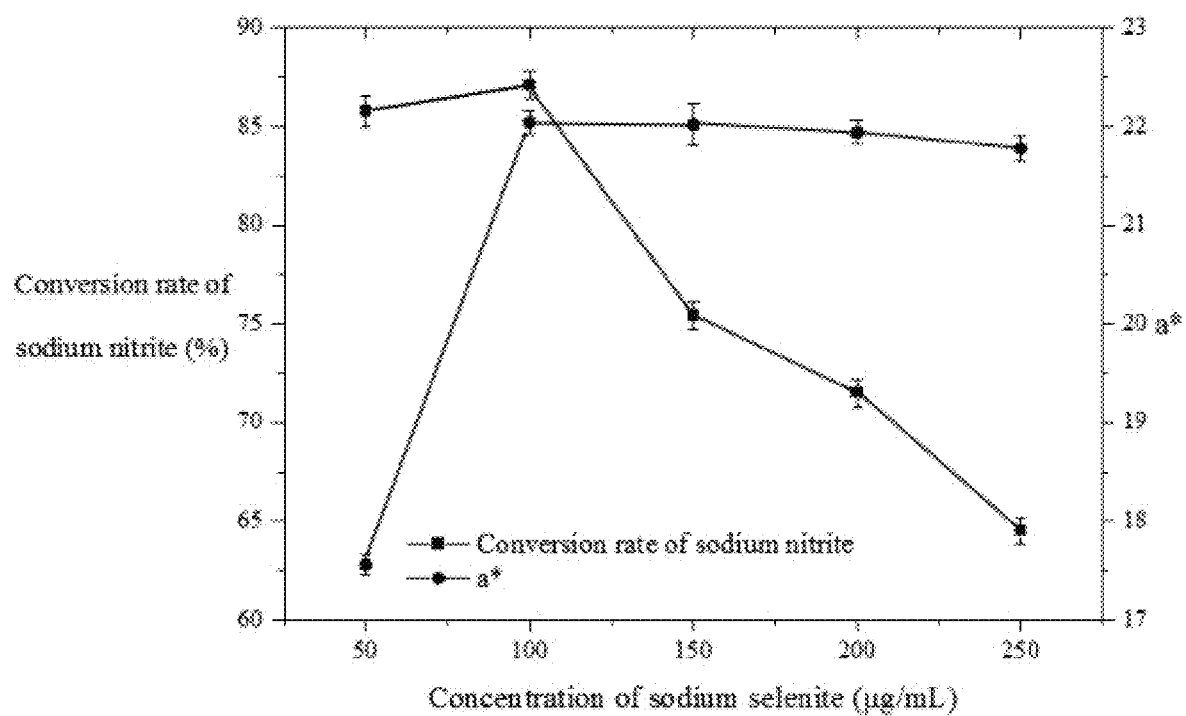
FIG. 5 shows the effects of different sodium selenite concentrations during the preparation of selenium-enriched *Lactiplantibacillus plantarum* KD-2.

As shown in FIG. 5, the conversion rate of sodium selenite first increases and then decreases with the concentration of sodium selenite. When the concentration of sodium selenite is 100 μg/mL, the conversion rate of sodium selenite reaches the maximum of 87.1%. When the concentration of sodium selenite is greater than 100 μg/mL, the conversion rate of sodium selenite gradually decreases, mainly because the reduction of sodium selenite is mainly affected by related reductases in bacteria. When there is too much sodium selenite, the bacteria are saturated with sodium selenite conversion, and sodium selenite inhibits the activity of the bacteria and reduces the activity of related enzyme actions. When the concentration of sodium selenite is 100-250 μg/mL, the a* red value changes gently, which is 22.04, 22.02, 21.94 and 21.78 respectively, indicating that the transformation ability of *Lactiplantibacillus plantarum* KD-2 to sodium selenite will not be enhanced because of the increase of sodium selenite. Therefore, the conversion rate of ≥70% and the a* red value≥20 are selected as appropriate indicators, and the corresponding sodium selenite concentration of 100-200 μg/mL is used as the appropriate concentration for the preparation of nano-selenium by transformation of *Lactiplantibacillus plantarum* KD-2.

5. Effect of *Lactiplantibacillus plantarum* KD-2 Addition on Preparation of nano-selenium Additions of *Lactiplantibacillus plantarum* KD-2 in the bacterial suspension are adjusted to be 0.02, 0.03, 0.04, 0.05, and 0.06 g/mL, and the concentration of sodium selenite is 100 μg/mL, and the pH value of the bacterial suspension is 7. The bacterial suspension is transformed at a constant temperature of 37° C. for 48 h, and the effect of the additions of *Lactiplantibacillus plantarum* KD-2 on the preparation of nano-selenium is analyzed, and the results are shown in FIG. 6.

Figure 6:
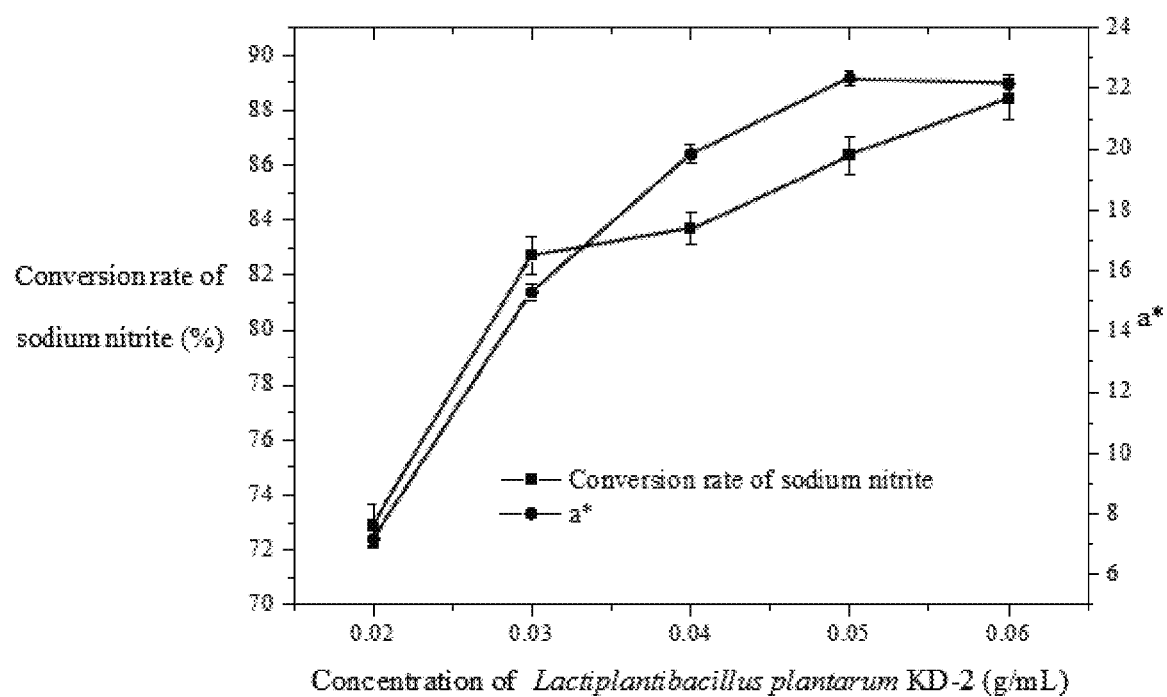
FIG. 6 shows the effect of *Lactiplantibacillus plantarum* KD-2 addition on the preparation of selenium-enriched *Lactiplantibacillus plantarum* KD-2.

As shown in FIG. 6, with the gradual increase of the addition of *Lactiplantibacillus plantarum* KD-2, the reduction conversion rate of sodium selenite increases gradually, and when the addition of *Lactiplantibacillus plantarum* KD-2 reaches 0.06 g/mL, the conversion rate of sodium selenite reaches a maximum of 88.44%. It indicates that when the concentration of sodium selenite is certain, the more the bacteria are added, the stronger the reduction ability of the bacteria is. From the a* red value, it is clear that when the addition amount of bacteria is 0.05 g/mL and 0.06 g/mL, the a* red value reaches 22.35 and 22.14, indicating that there is no significant difference in the red degree of the bacterial suspension when the addition amount of bacteria is 0.05 g/mL and 0.06 g/mL, taking into account the economic practicability, the addition amount of *Lactiplantibacillus plantarum* KD-2 is subsequently selected to be 0.05 g/mL.

6. Optimization of Preparation Conditions of Selenium-Enriched *Lactiplantibacillus Plantarum* KD-2 by Response Surface Methodology According to the results of single factor, the changes of reaction duration, temperature, pH value, concentration of sodium selenite and the amount of bacteria all have different effects on the preparation of nano-selenium by *Lactiplantibacillus plantarum* KD-2, among which the changes of duration and the addition amount of *Lactiplantibacillus plantarum* KD-2 have greater influence on the conversion rate of sodium selenite, followed by pH and temperature, and the amount of sodium selenite has the least influence. Therefore, the transformation duration, the addition amount of *Lactiplantibacillus plantarum* KD-2 and pH are selected as variables, and the conversion rate of sodium selenite (%), the content of nano-selenium per unit cell (mg/g) and the a* red value are taken as response values. The central composite design with three factors and five levels is adopted to optimize the process parameters for preparing nano-selenium. The factor level, experimental design and results are shown in Tables 1 and 2.

TABLE 1

Table of factors for optimizing the preparation of selenium-enriched *Lactiplantibacillus plantarum* KD-2 by central composite experiment

| Serial number | -1.68 | -1 | 0 | 1 | 1.68 |
|---|---|---|---|---|---|
| A Duration (h) | 44.64 | 46 | 48 | 50 | 51.36 |
| B *Lactiplantibacillus plantarum* KD-2 addition (g/mL) | 0.33 | 0.04 | 0.05 | 0.06 | 0.067 |
| C pH | 6.66 | 6.8 | 7.0 | 7.2 | 7.34 |

TABLE 2

Experimental design and results of optimizing the preparation of selenium-enriched *Lactiplantibacillus plantarum* KD-2 by central composite experiment

| Run | A | B | C | R1 (Conversion rate) | R2 (Nano-selenium content per unit of bacterium) | R3 (a* red value) |
|---|---|---|---|---|---|---|
| 1 | 0.000 | 0.000 | 0.000 | 97.35 | 1.173 | 28.69 |
| 2 | -1.682 | 0.000 | 0.000 | 95.58 | 0.995 | 23.36 |
| 3 | 0.000 | -1.682 | 0.000 | 82.17 | 0.960 | 23.80 |
| 4 | 0.000 | 0.000 | 0.000 | 97.29 | 1.322 | 27.11 |
| 5 | 1.682 | 0.000 | 0.000 | 96.00 | 0.980 | 23.52 |
| 6 | -1.000 | -1.000 | 1.000 | 91.40 | 0.981 | 22.28 |
| 7 | 0.000 | 0.000 | 1.682 | 94.55 | 0.991 | 25.12 |
| 8 | 0.000 | 0.000 | 0.000 | 96.69 | 1.105 | 27.28 |
| 9 | 0.000 | 1.682 | 0.000 | 94.08 | 0.971 | 24.12 |
| 10 | 1.000 | -1.000 | -1.000 | 88.51 | 0.967 | 23.28 |
| 11 | -1.000 | 1.000 | 1.000 | 94.04 | 0.937 | 23.50 |
| 12 | 1.000 | -1.000 | 1.000 | 84.83 | 0.891 | 22.10 |
| 13 | -1.000 | -1.000 | -1.000 | 88.47 | 0.985 | 23.09 |
| 14 | 0.000 | 0.000 | 0.000 | 97.51 | 1.287 | 27.37 |
| 15 | 0.000 | 0.000 | 0.000 | 94.83 | 1.267 | 26.26 |
| 16 | 0.000 | 0.000 | -1.682 | 95.70 | 0.980 | 24.19 |
| 17 | 0.000 | 0.000 | 0.000 | 94.68 | 1.268 | 26.56 |
| 18 | 1.000 | 1.000 | 1.000 | 98.07 | 0.890 | 21.53 |
| 19 | -1.000 | 1.000 | -1.000 | 95.96 | 0.912 | 23.13 |
| 20 | 1.000 | 1.000 | -1.000 | 98.04 | 0.989 | 24.44 |

According to the test results in Table 1, the regression equation is constructed as follows:

$$R1 = 96.4 + 0.021A + 3.88B - 0.33C +$$
$$1.58AB - 0.58AC - 0.14BC - 3.01A^2 - 3.01B^2 - 0.53C^2;$$

$$R2 = 1238.067.72A - 5.63B - 10.17C + 17.06AB -$$
$$24.37AC + 0.84BC - 92.4A^2 - 100.33B^2 + 93.17C^2; \text{ and}$$

$$R3 = 27.24 - 0.028A + 0.17B - 0.22C -$$
$$0.084AB - 0.46AC - 0.069BC - 1.52A^2 - 1.34B^2 - 1.10C^2.$$

In the equations, R1, R2 and R3 are the predicted values of sodium selenite conversion rate, nano-selenium content per unit cell and a* red value respectively. A, B and C represent duration, addition of *Lactiplantibacillus plantarum* KD-2 and pH respectively.

The contour lines and three-dimensional response surface diagrams of the effects of pH, duration and the addition of *Lactiplantibacillus plantarum* KD-2 on the conversion rate, the content of nano-selenium per unit cell and the a* red value are shown in FIG. 8A-FIG. 8F, FIG. 9A-FIG. 9F, and FIG. 10A-FIG. 10F.

Combined with the previous single-factor test and Table 2, it is found that at the addition of sodium selenite of 100-200 μg/mL, *Lactiplantibacillus plantarum* KD-2 of 0.033-0.067 mg/mL, pH of 6.66-7.34, transformation temperature of 35-39° C., and transformation duration of 44 h-51 h, the conversion rate is 82.17%-98.07%, the nano-selenium content per unit of bacterium is 0.890 mg/g-1.322 mg/g, and the a* red value is 21.53-28.69.

Through the analysis of regression equations, the predicted values of the best technological parameters for the preparation and transformation conditions of selenium-enriched *Lactiplantibacillus plantarum* KD-2 are obtained. The predicted optimum technological conditions are pH 6.98, the addition of bacterial sludge 0.052 g/mL, and the transformation duration 48 h. Under these conditions, the transformation rate is 97.07%, the selenium content per unit cell is 1.23 mg/g, and the a* red value is 28.69. The pH value is adjusted to 7 for the experimental operation convenience, and the verification experiment is carried out. Under this condition, the conversion rate reaches (96.57±1.24%), the selenium content per unit cell is (1.21±0.15) mg/g, and the a* red value is (27.32±0.105). The actual values are very close to the predicted values, indicating that the optimization of the process for the preparation of nano-selenium by *Lactiplantibacillus plantarum* KD-2 using a combinatorial experimental design is feasible.

Calomme et al. investigated the selenium content in the cells of three strains of *Lactiplantibacillus plantarum, L. delbrueckii* ssp *bulgaricus* and *L. casei* ssp after culturing in medium enriched with 1 mg/L $Na_2SeO_3$, which were 0.375, 0.253 and 0.407 mg/g, respectively, lower than the content of 1.21 mg/g of selenium per unit bacterium obtained by *Lactiplantibacillus plantarum* KD-2 under optimal process conditions. This is mainly because the *Lactobacillus plantarum* KD-2 in this experiment is collected directly for biotransformation to prepare nano-selenium after the organisms are grown in the medium to the logarithmic phase when the organisms are no longer growing, at this time the enzyme activity in the organisms is higher and the organisms are less inhibited by the sodium selenite, so more sodium selenite will be reduced. This also indicates that direct biotransformation of the well-grown organisms to reduce sodium selenite is more efficient than reducing sodium selenite while growing in the medium containing it.

Embodiment 4 Selenium-Enriched *Lactiplantibacillus plantarum* KD-2 Powder

The transformation solution obtained in Embodiment 3 is used as raw material, and it is frozen and centrifuged (centrifugation condition is 12000 r/min, 4° C., 15 min) to obtain selenium-enriched *Lactiplantibacillus plantarum* KD-2 precipitate, which is washed with 0.85% saline to remove sodium selenite in the precipitate, and it is centrifuged again to obtain selenium-enriched *Lactiplantibacillus plantarum* KD-2 precipitate; then, 40 g of monosodium glutamate, 25 g of sodium ascorbate, 30% of skimmed milk 1 L, 250 mL of phosphate buffer and 4 drops of Tween 80 are added according to the weight of precipitation, and then mixed well with a vortex mixer, and then placed in a lyophilized tray with the loading height of 0.5 cm, and then placed into the −35° C. environment to be pre-frozen for 5 h, then freeze-dried at −55° C. under vacuum of 5 Pa for 24 h to obtain selenium-enriched *Lactiplantibacillus plantarum* KD-2 powder. The number of viable bacteria is $1.22 \times 10^{11}$ CFU/g, and the inactivation rate constant of *Lactiplantibacillus plantarum* KD-2 in selenium-enriched *Lactiplantibacillus plantarum* KD-2 powder is $1.82 \times 10^{-6}$ by accelerated test, which shows that the activity is stable.

Figure 7A:
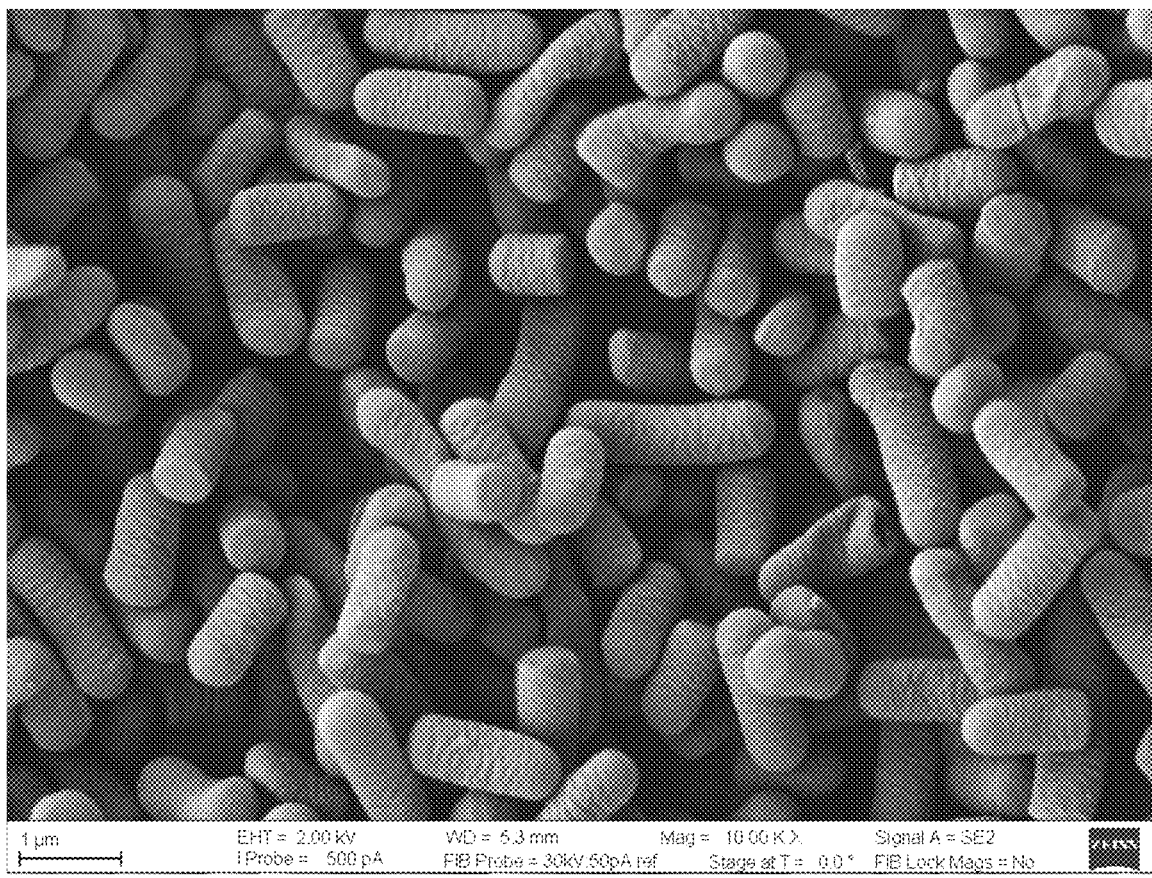
FIG. 7A is the SEM picture of the strain before transformation.
Figure 7B:
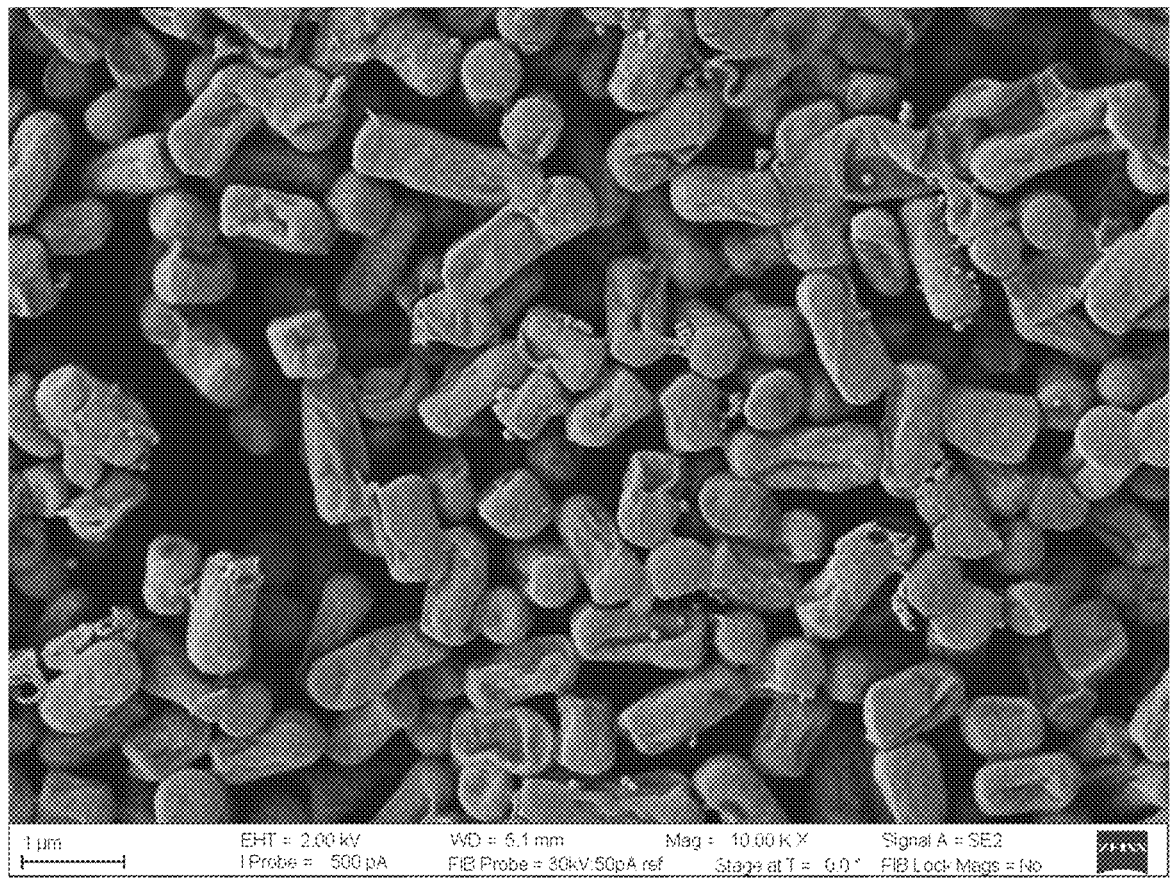
FIG. 7B is the SEM picture of the transformed strain.
Figure 7C:
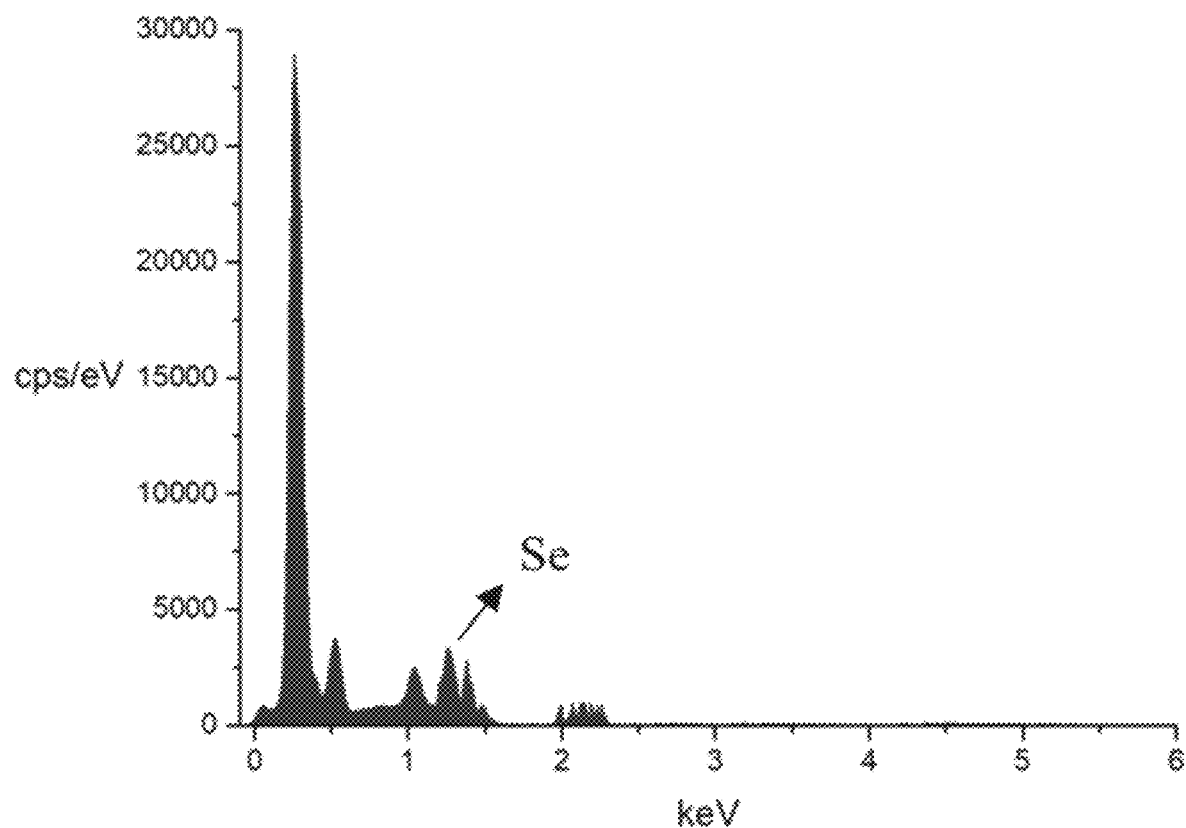
FIG. 7C is the EDX analysis picture of small particles.
Figure 8A:
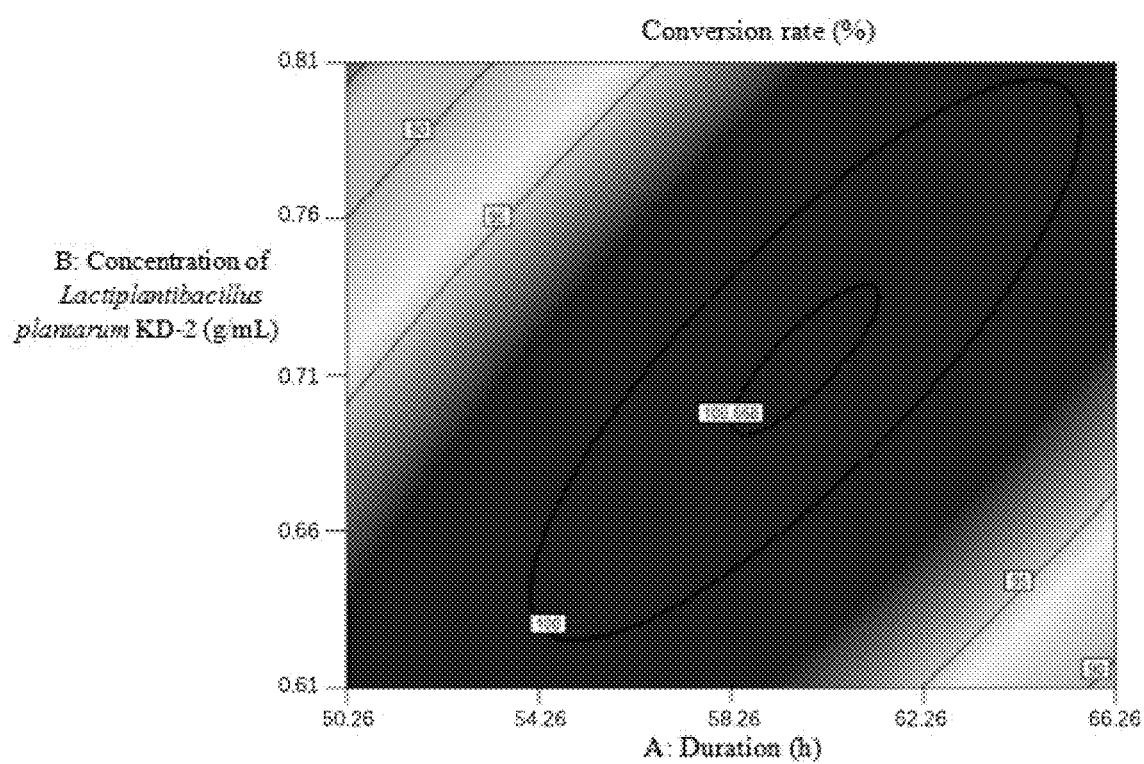
FIG. 8A is the contour plot of the effects of duration and *Lactiplantibacillus plantarum* KD-2 concentration on the conversion rate of sodium selenite.
Figure 8B:
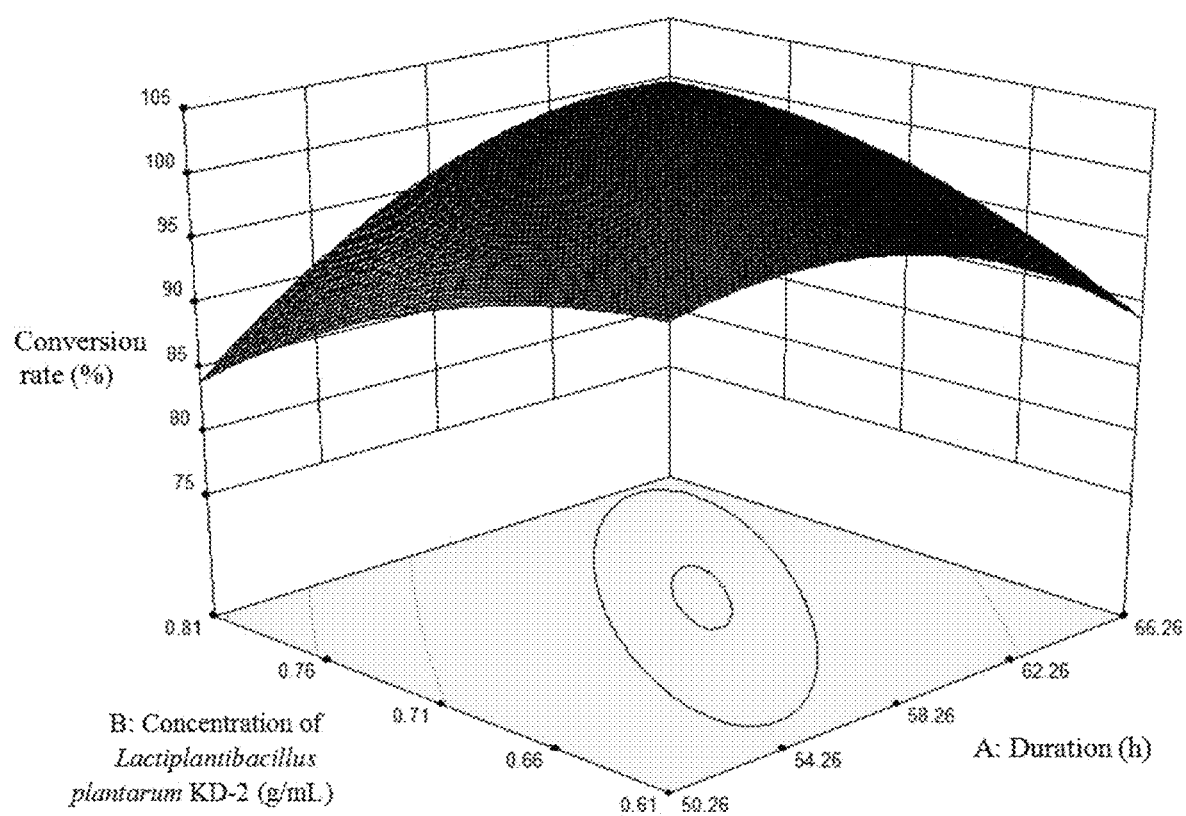
FIG. 8B is the response surface plot of the effects of duration and *Lactiplantibacillus plantarum* KD-2 concentration on the conversion rate of sodium selenite.
Figure 8C:
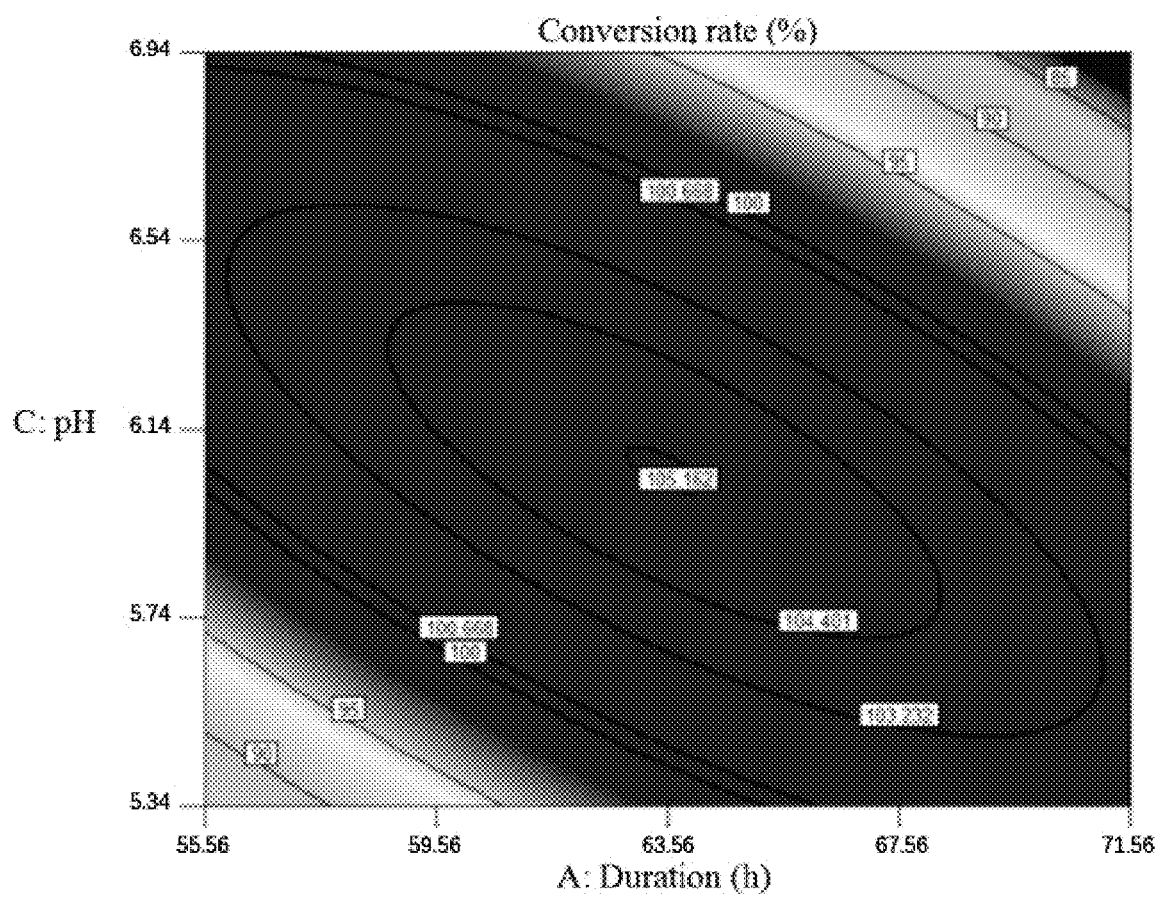
FIG. 8C is the contour plot of the effects of pH and duration on the conversion rate of sodium selenite.
Figure 8D:
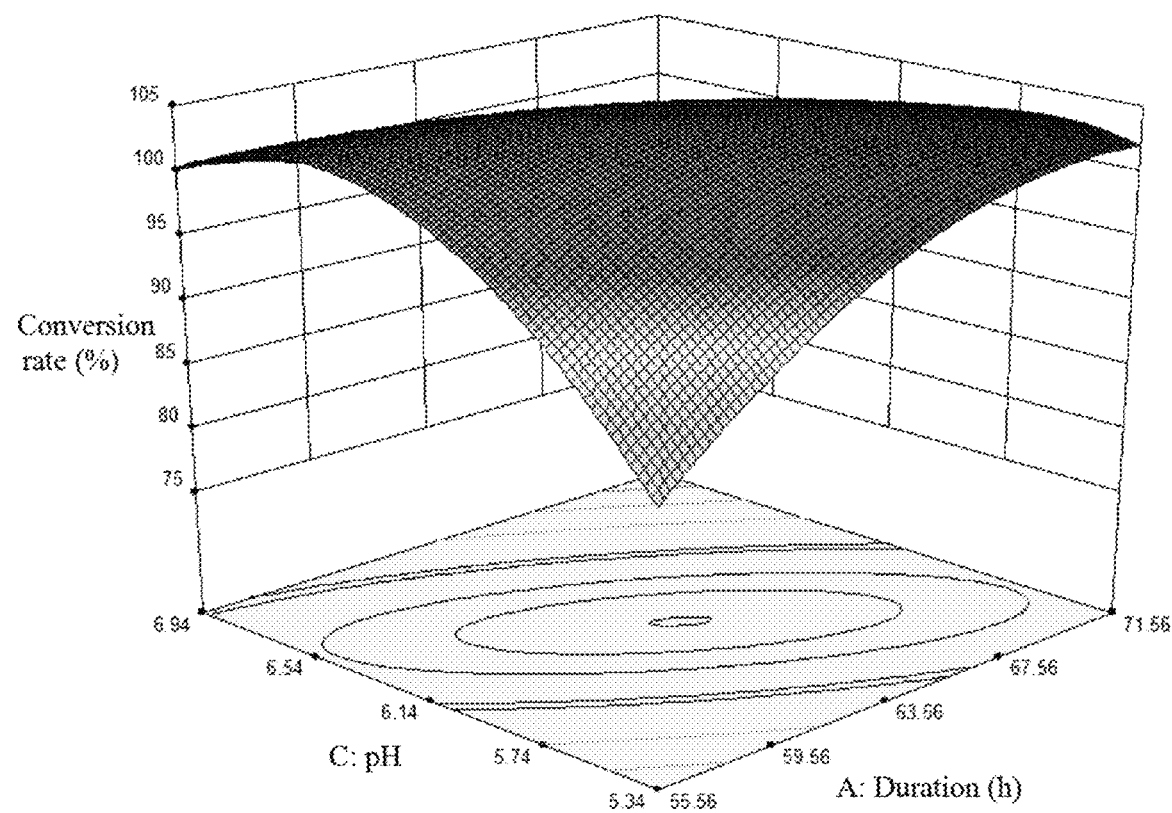
FIG. 8D is the response surface plot of the effects of pH and duration on the conversion rate of sodium selenite.
Figure 8E:
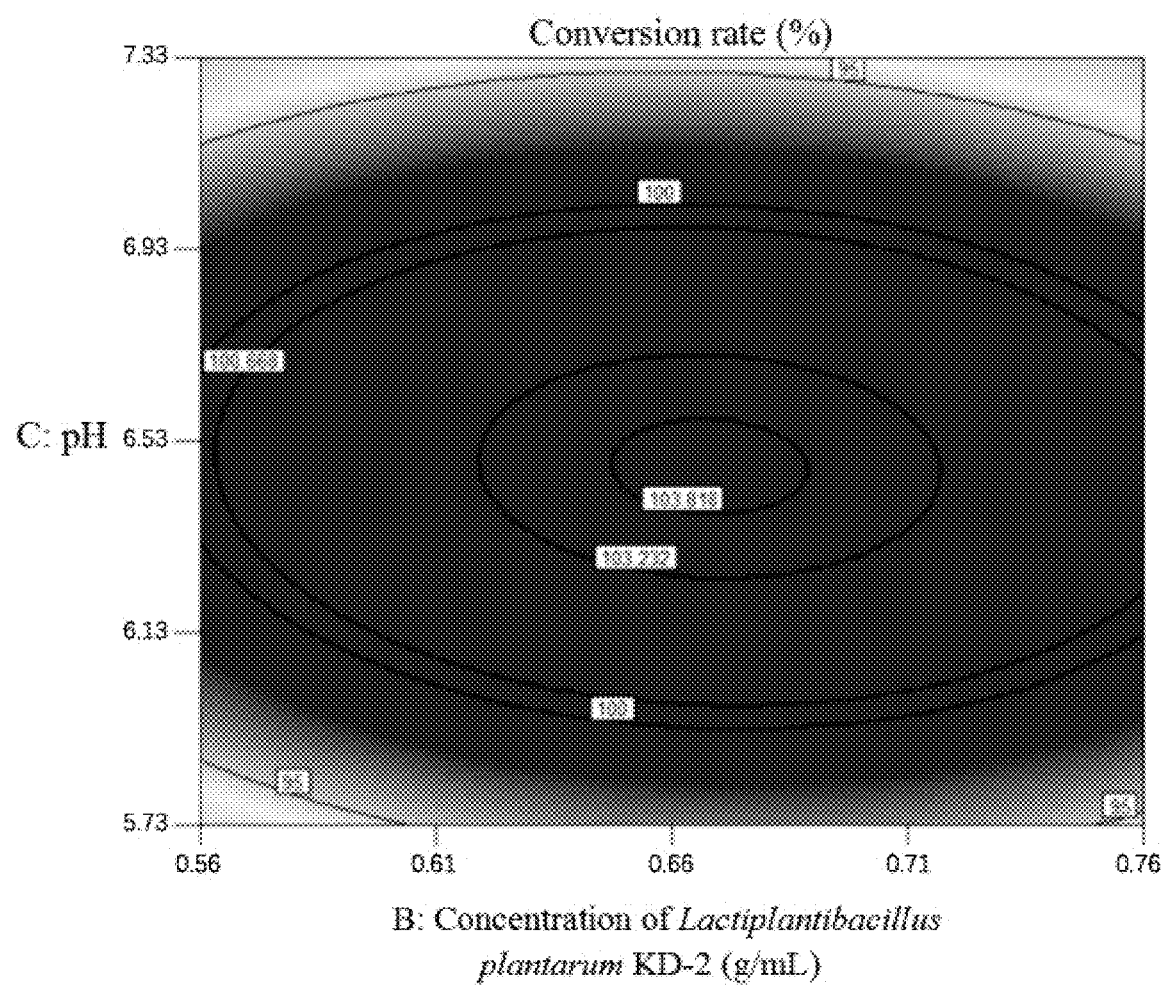
FIG. 8E is the contour plot the effects of pH and *Lactiplantibacillus plantarum* KD-2 concentration on the conversion rate of sodium selenite.
Figure 8F:
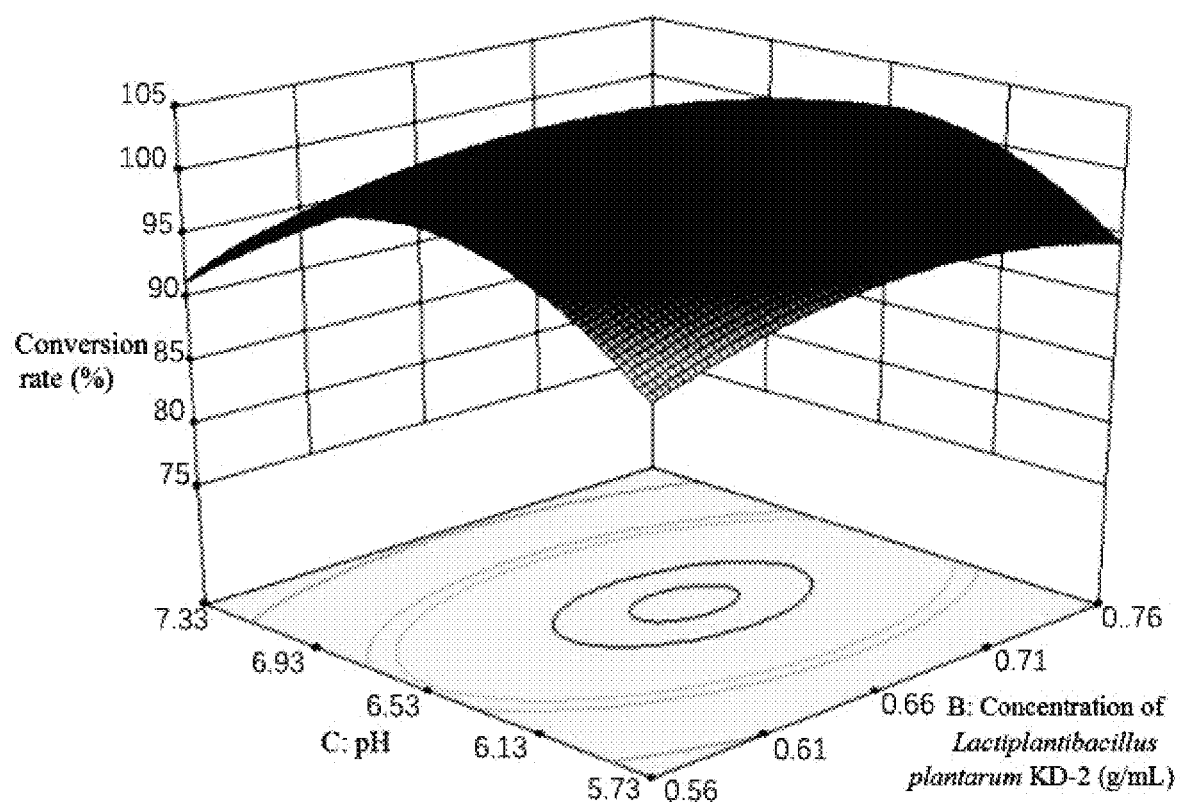
FIG. 8F is the response surface plot of the effects of pH and *Lactiplantibacillus plantarum* KD-2 concentration on the conversion rate of sodium selenite.
Figure 9A:
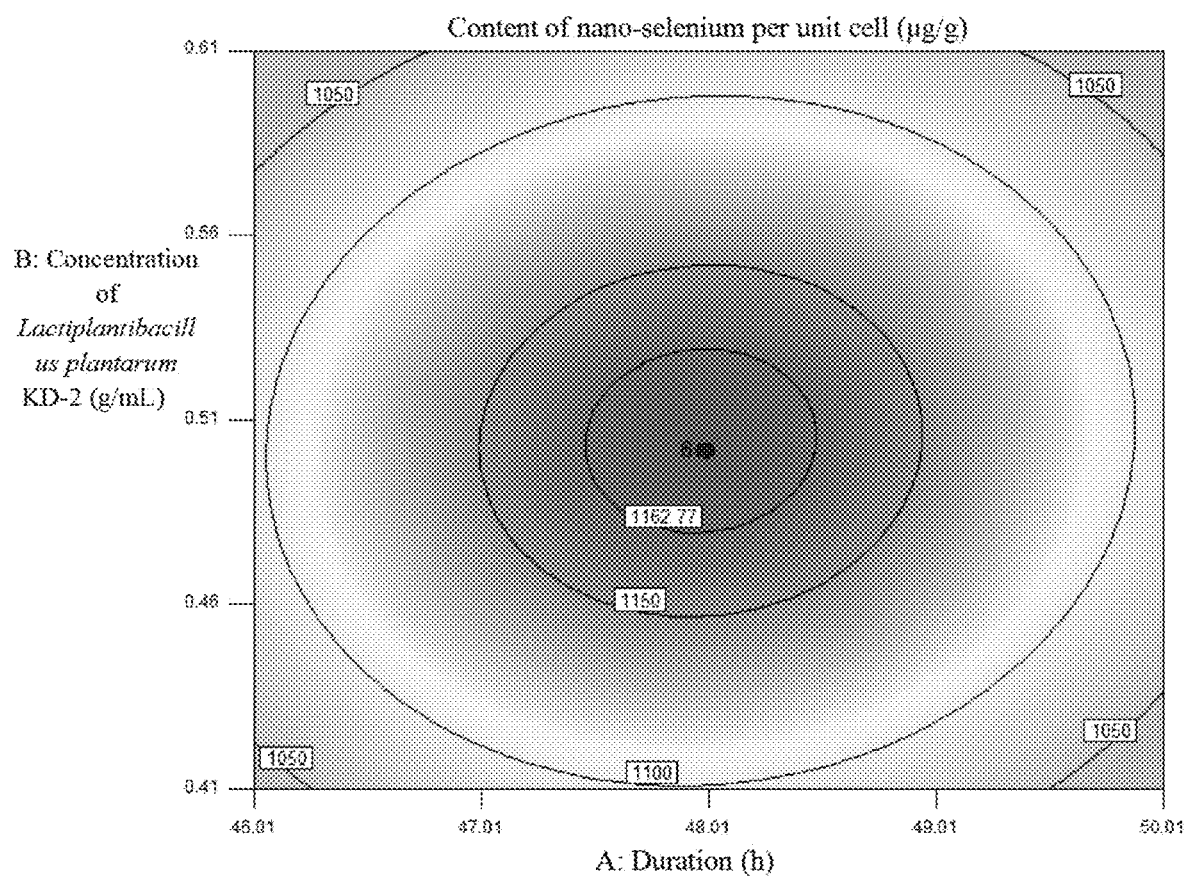
FIG. 9A is contour plot of the effects of duration and *Lactiplantibacillus plantarum* KD-2 concentration on selenium content per unit cell.
Figure 9B:
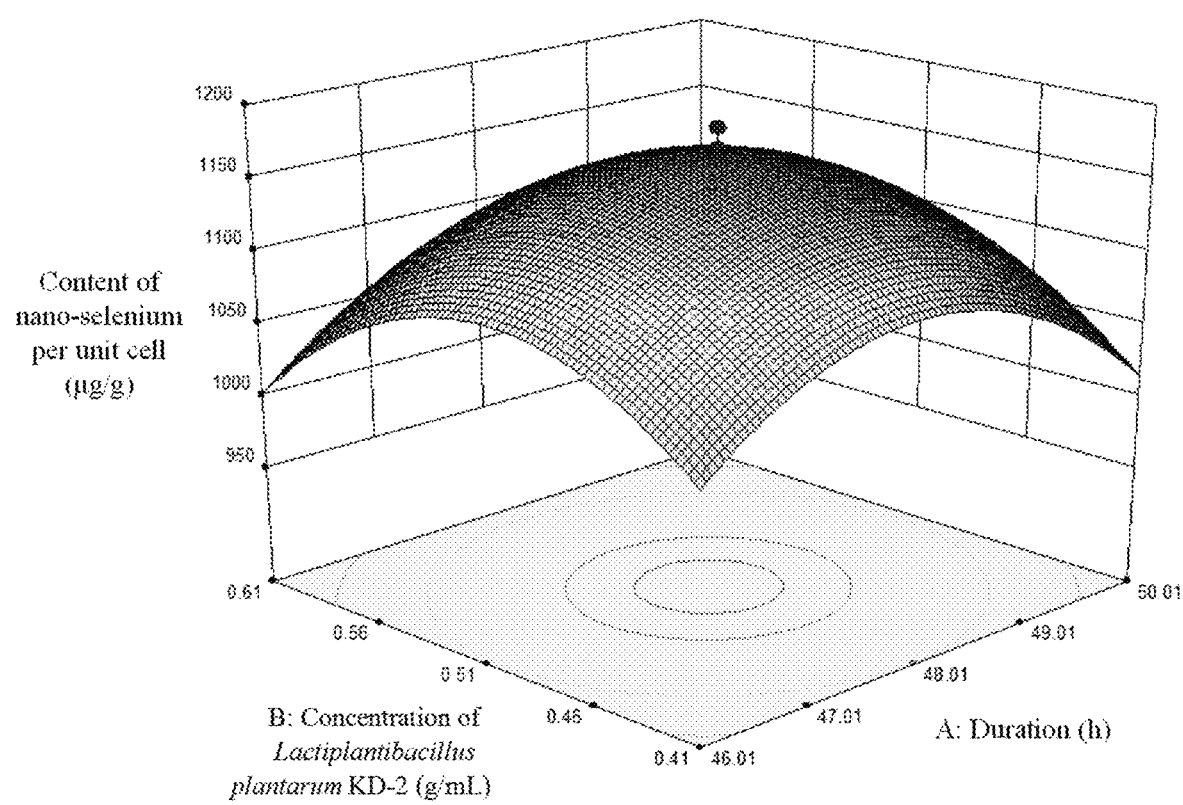
FIG. 9B is response surface plot of the effects of duration and *Lactiplantibacillus plantarum* KD-2 concentration on selenium content per unit cell.
Figure 9C:
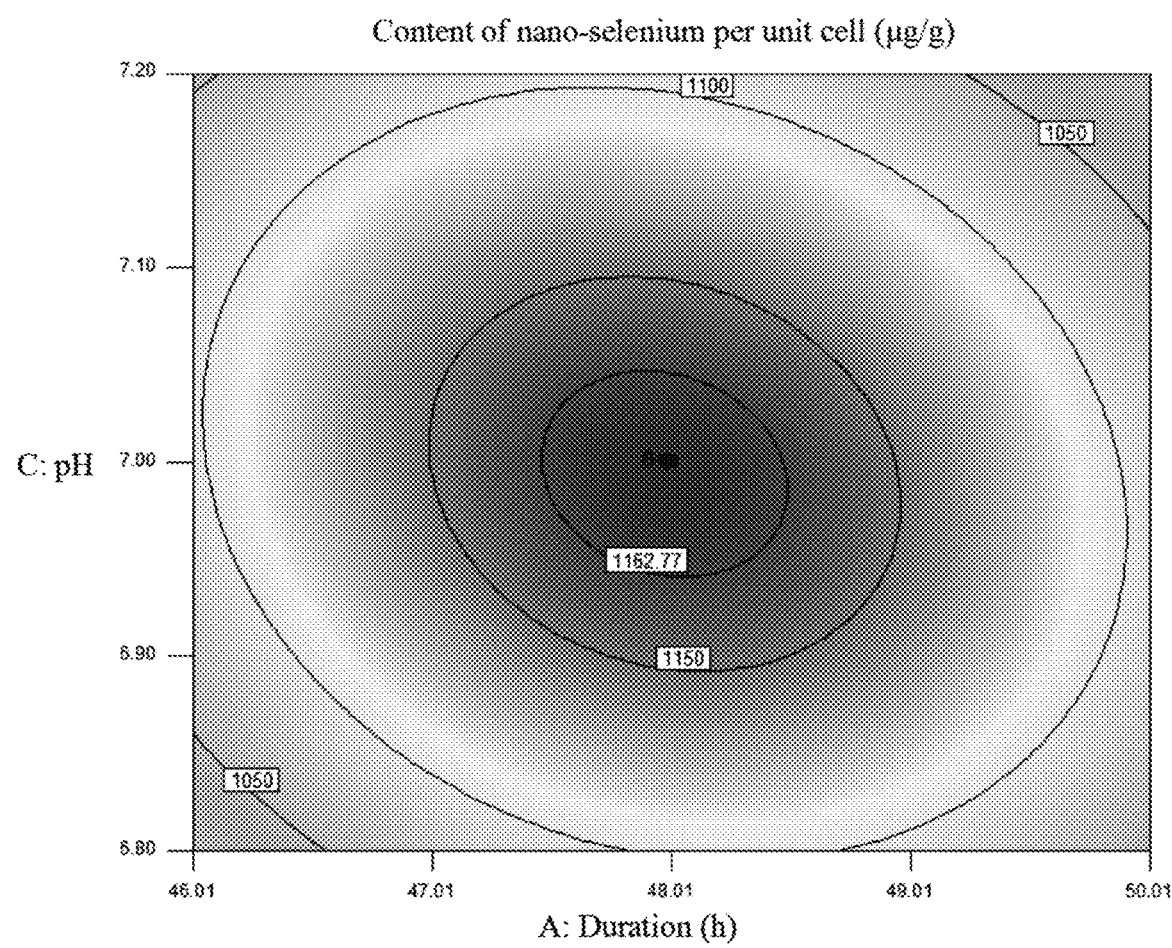
FIG. 9C is contour plot of the effects of pH and duration on selenium content per unit cell.
Figure 9D:
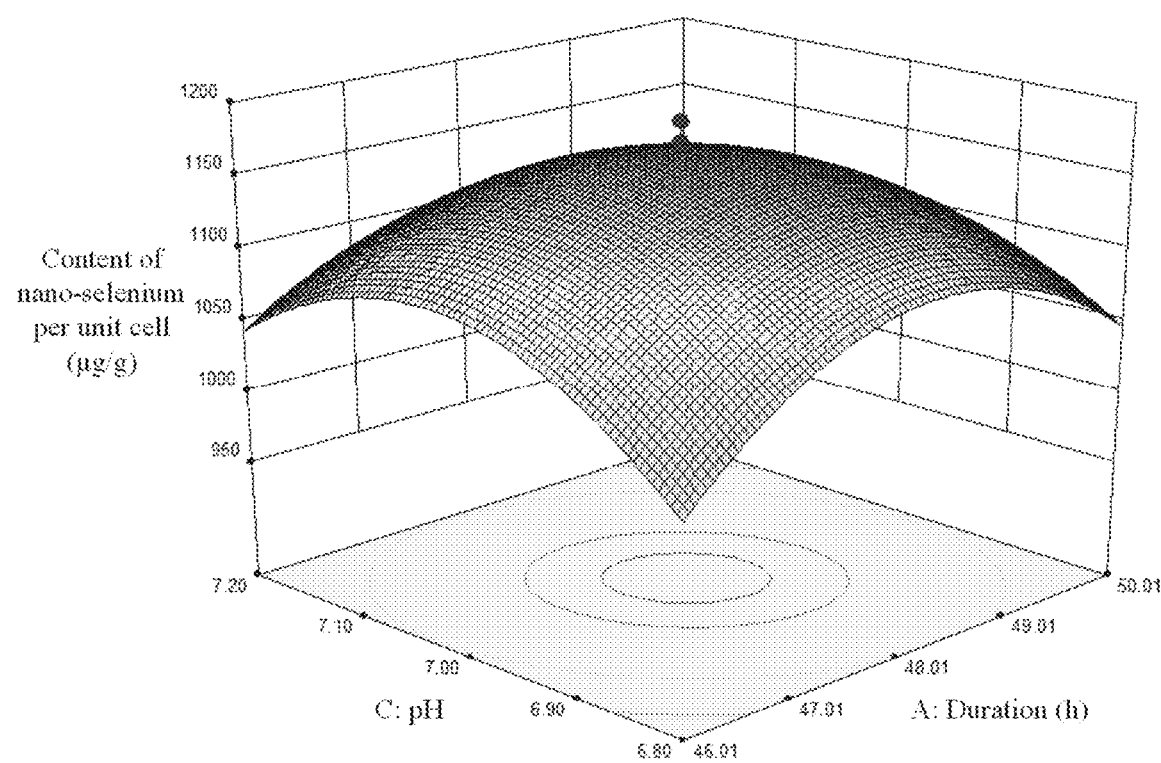
FIG. 9D is response surface plot of the effects of pH and duration on selenium content per unit cell.
Figure 9E:
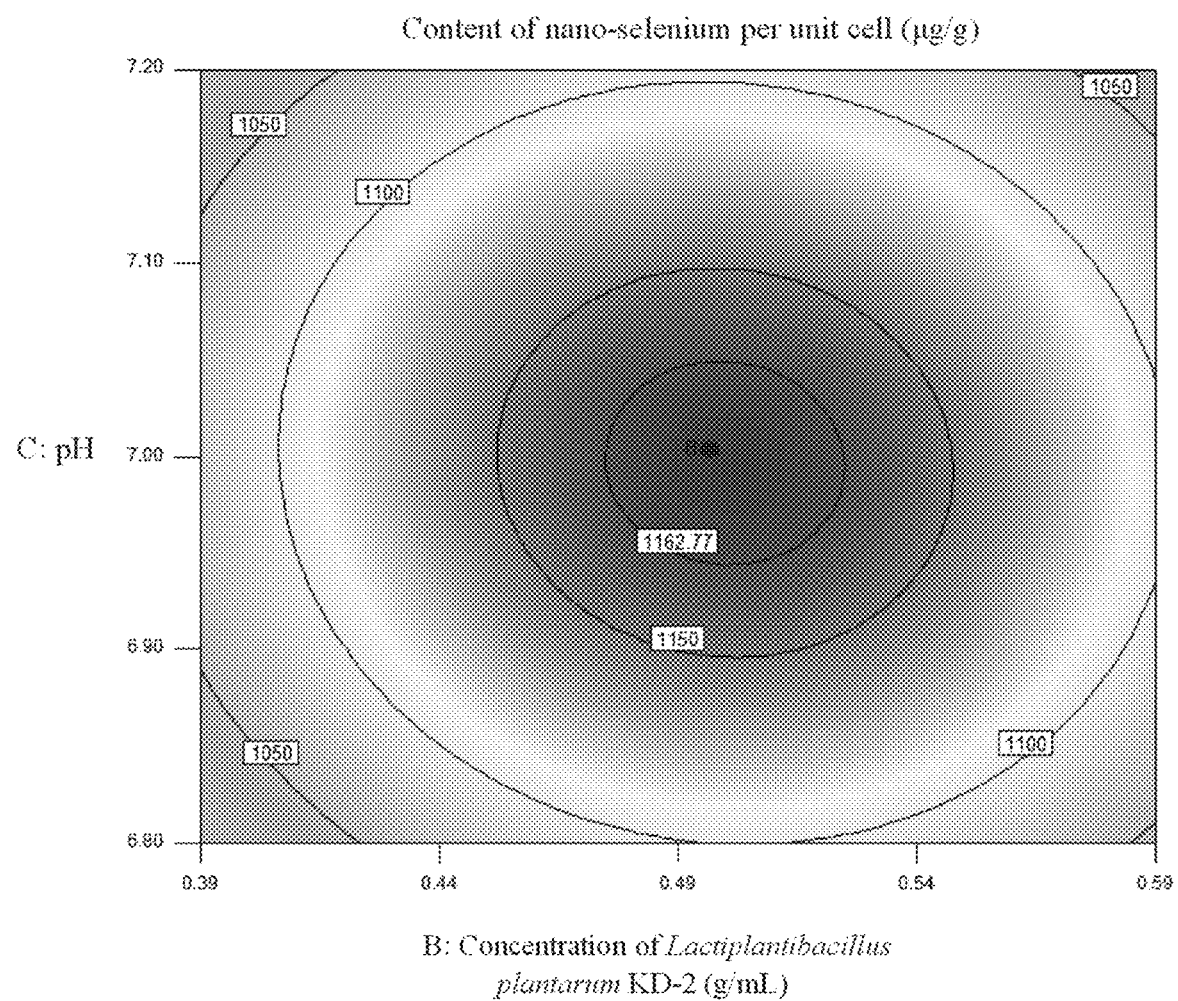
FIG. 9E is contour plot the effects of pH and *Lactiplantibacillus plantarum* KD-2 concentration on selenium content per unit cell.
Figure 9F:
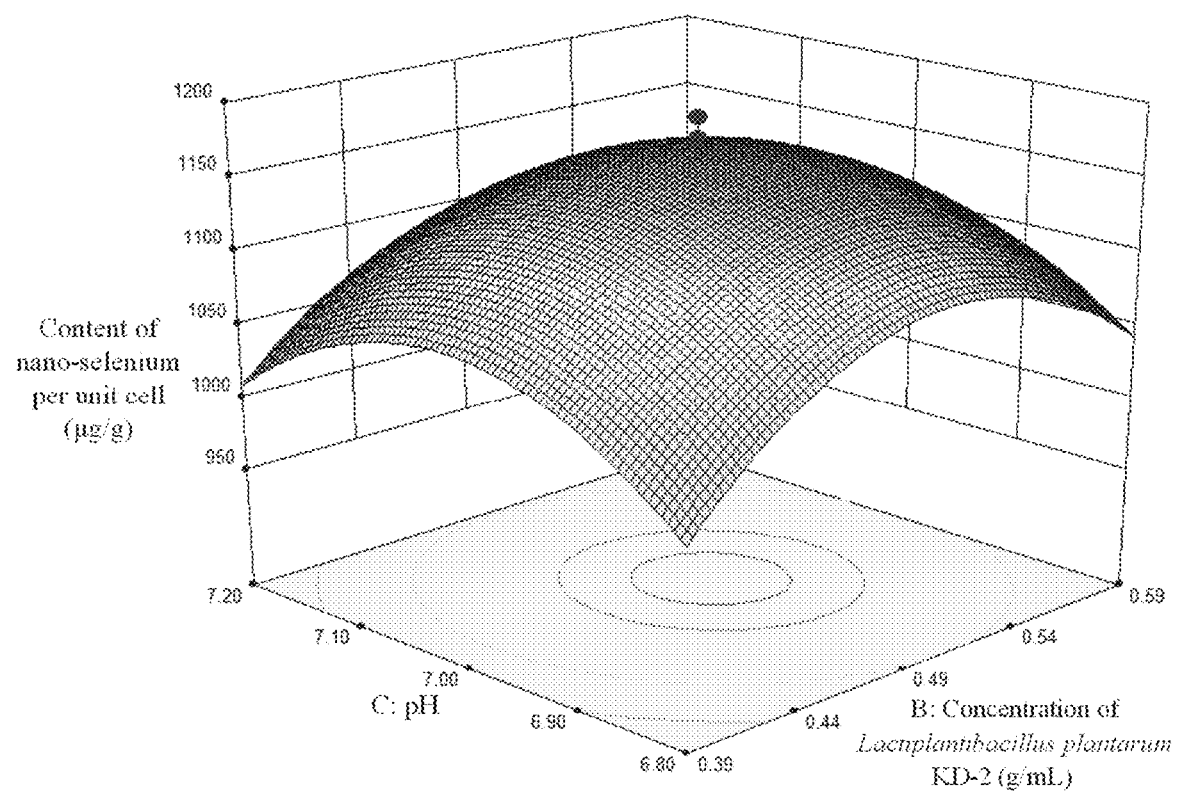
FIG. 9F is response surface plot of the effects of pH and *Lactiplantibacillus plantarum* KD-2 concentration on selenium content per unit cell.
Figure 10A:
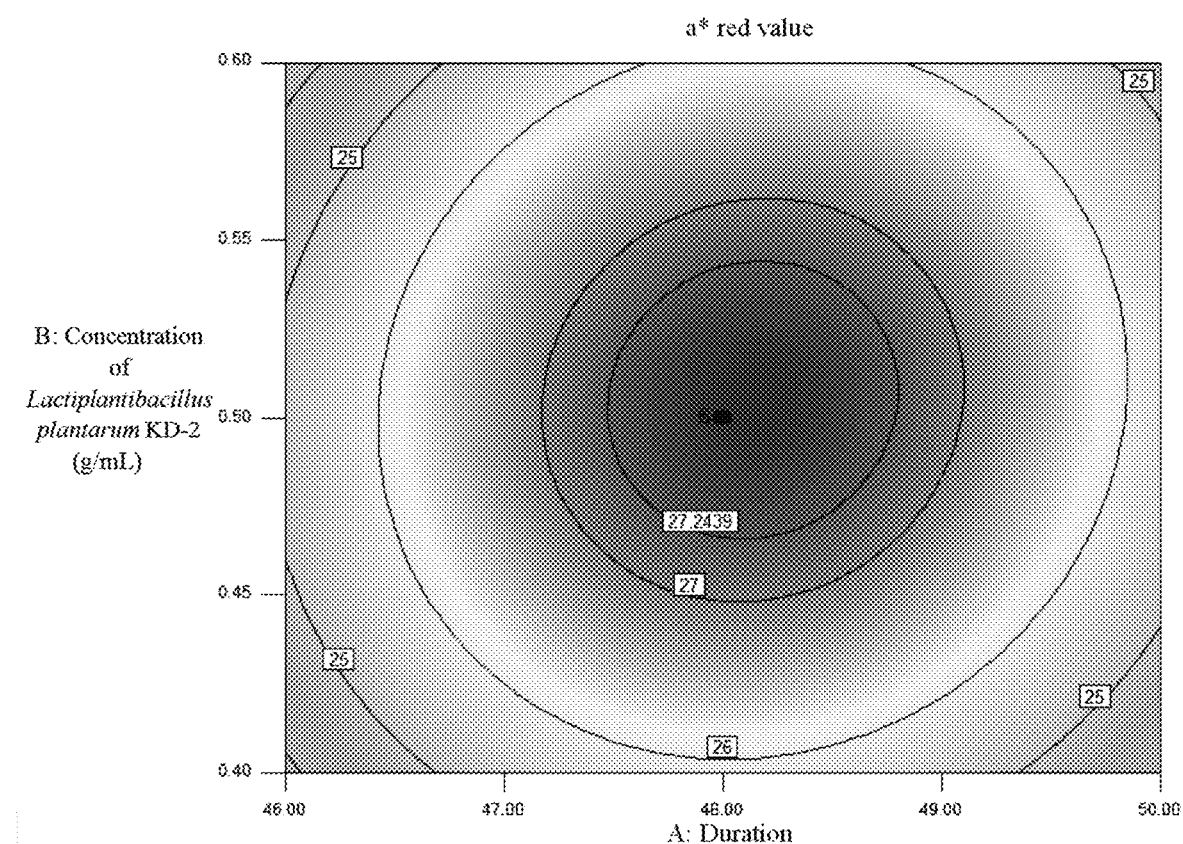
FIG. 10A is contour plot of the effects of duration and *Lactiplantibacillus plantarum* KD-2 concentration on a* red value.
Figure 10B:
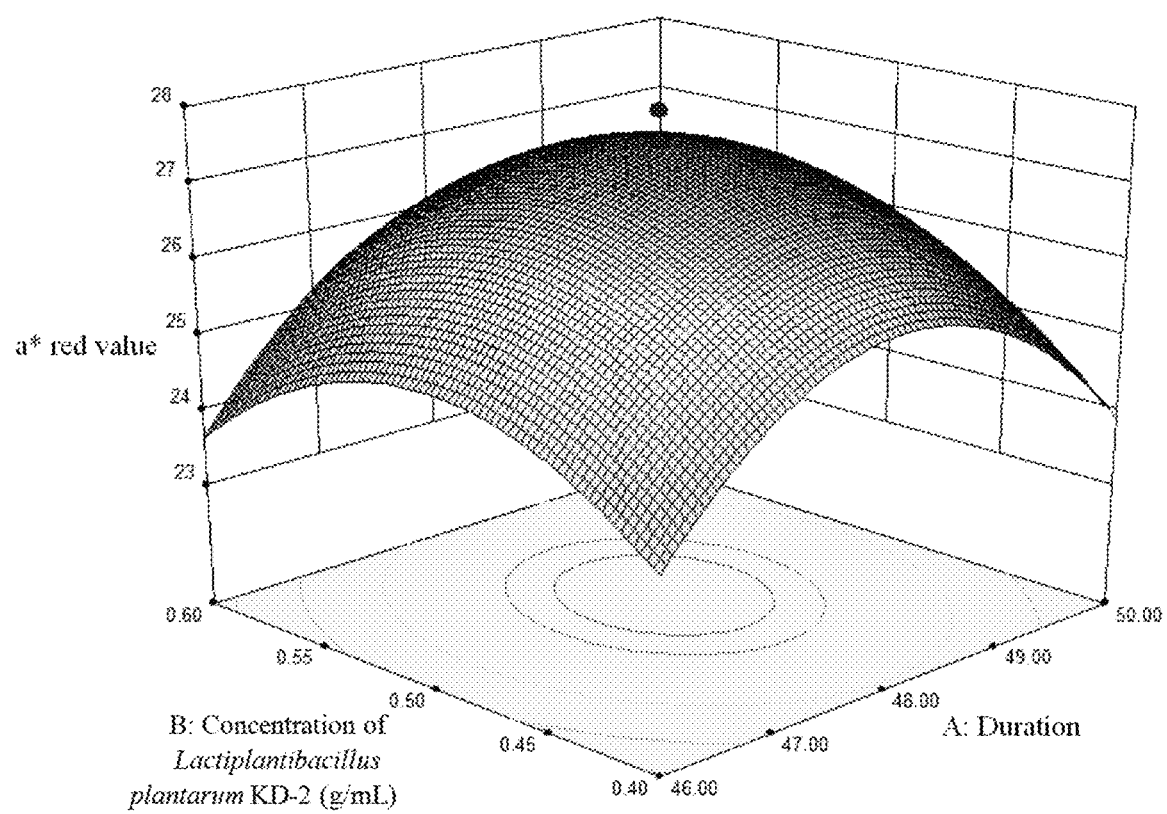
FIG. 10B is response surface plot of the effects of duration and *Lactiplantibacillus plantarum* KD-2 concentration on a* red value.
Figure 10C:
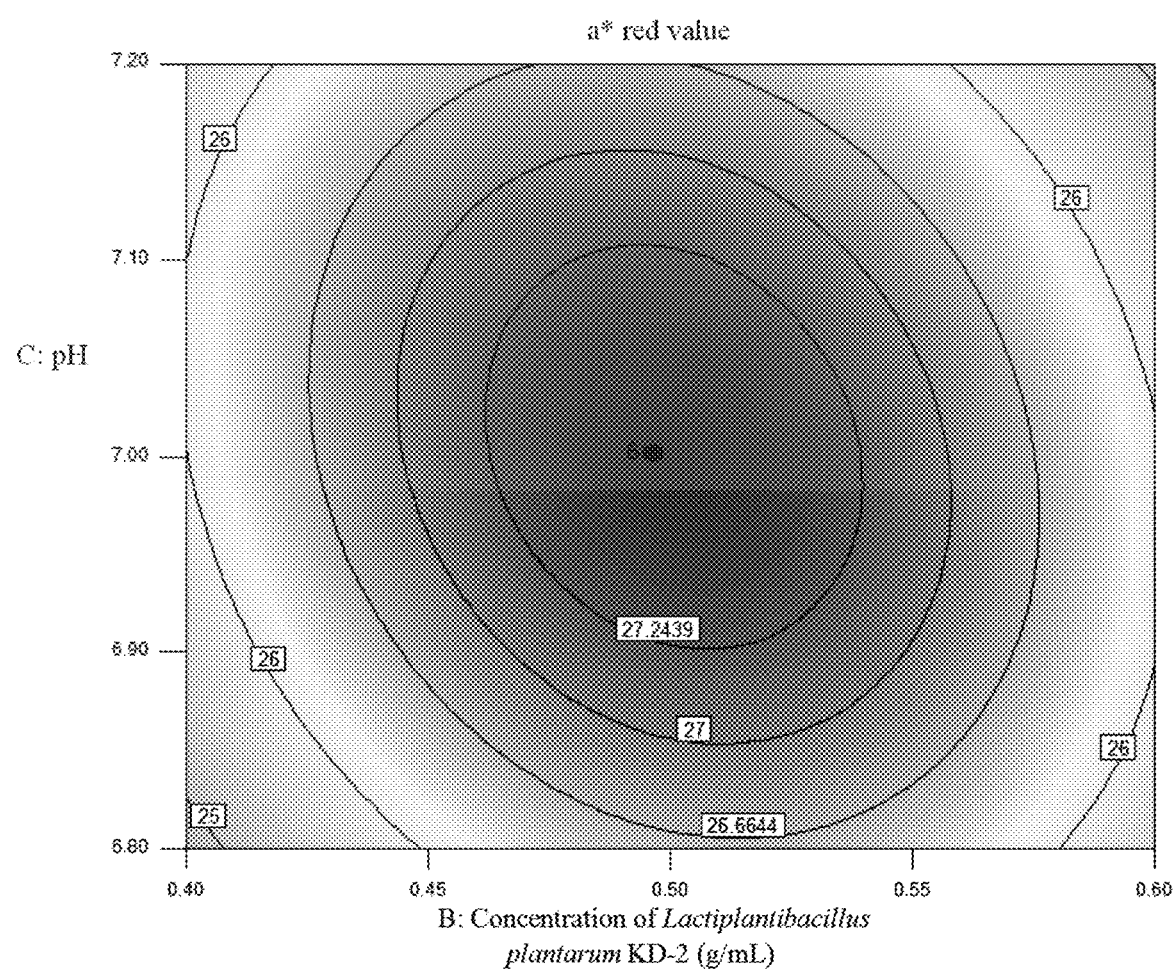
FIG. 10C is contour plot of the effects of pH and duration on a* red value.
Figure 10D:
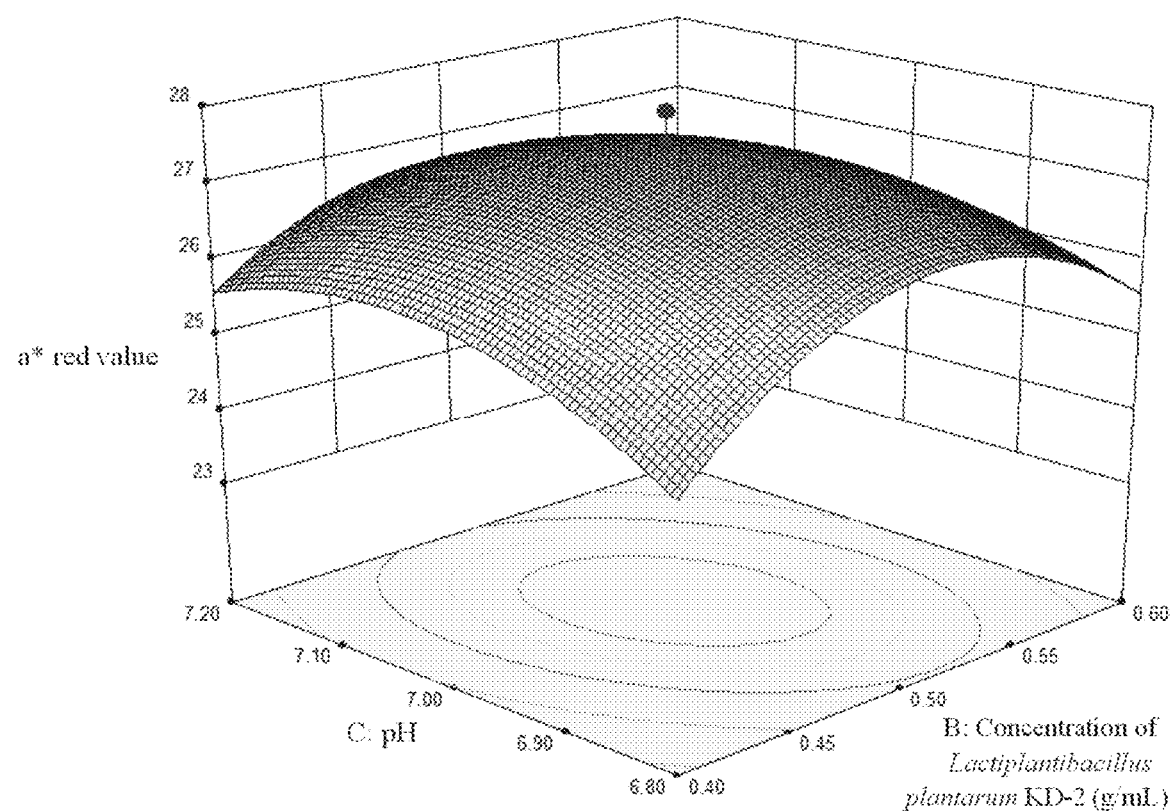
FIG. 10D is response surface plot of the effects of pH and duration on a* red value.
Figure 10E:
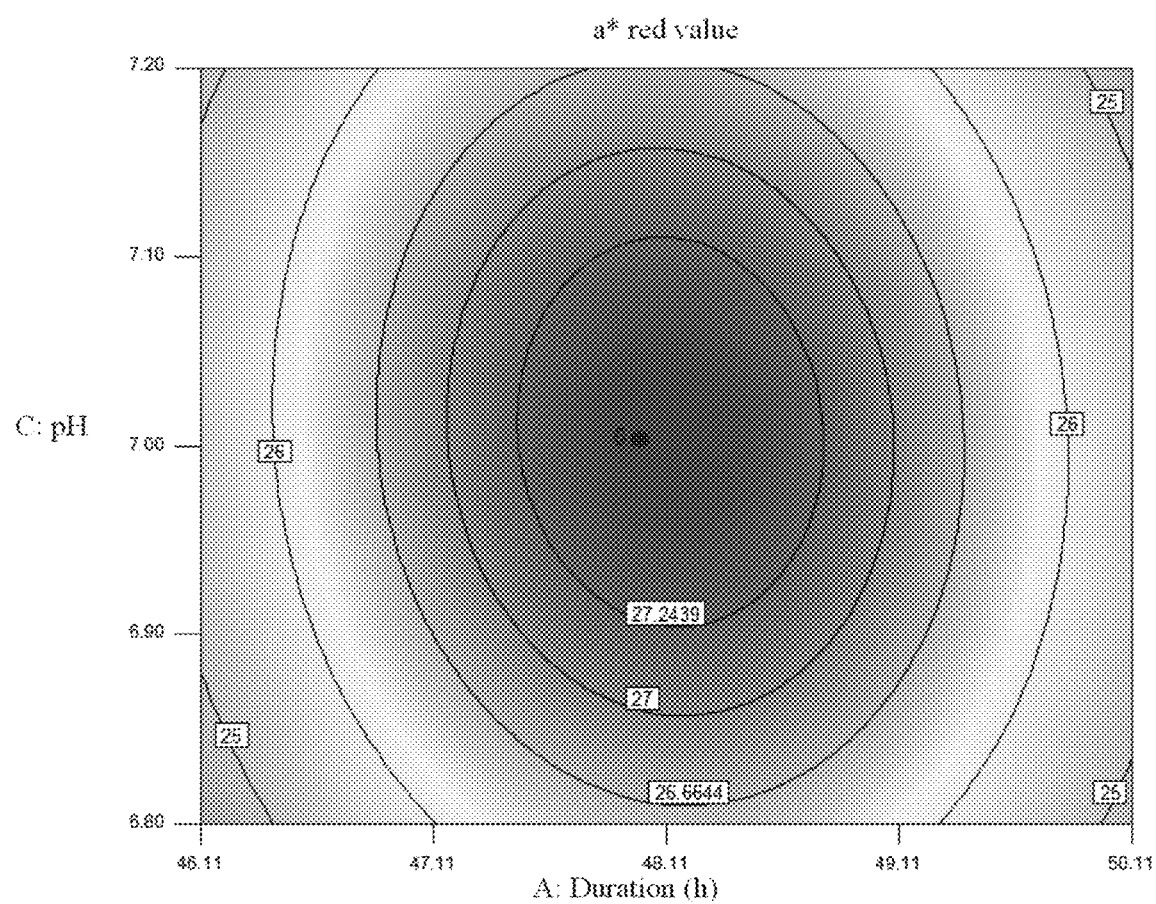
FIG. 10E is contour plot of the effects of pH and *Lactiplantibacillus plantarum* KD-2 concentration on a* red value.
Figure 10F:
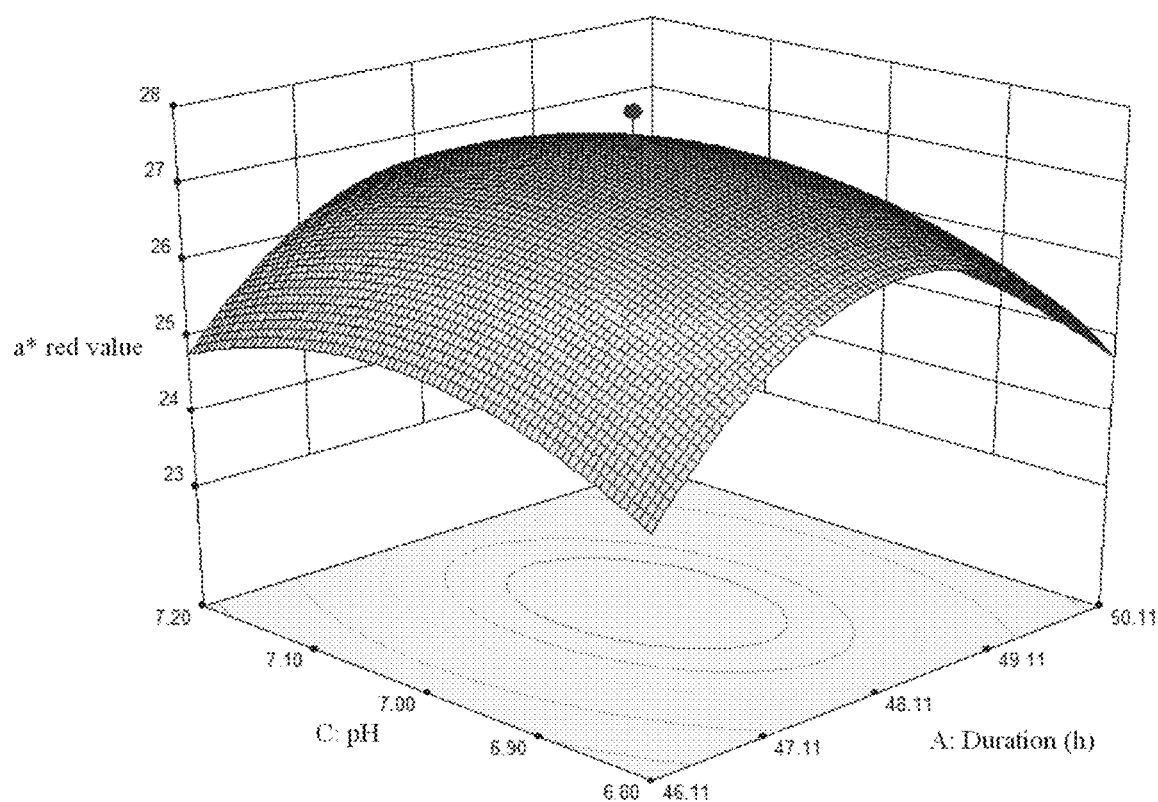
FIG. 10F is response surface plot of the effects of pH and *Lactiplantibacillus plantarum* KD-2 concentration on a* red value.

FIG. 7A-FIG. 7C show the scanning electron microscope photographs of *Lactiplantibacillus plantarum* KD-2 and *Lactiplantibacillus plantarum* KD-2 powder enriched with selenium. From FIG. 7A, it may be seen that *Lactiplantibacillus plantarum* KD-2 powder without sodium selenite is smooth and short rod-shaped. After sodium selenite is reduced, the surface of the bacteria appears invagination, shrinkage and eversion, and round nano-sized particles appear around it. The small particles in FIG. 7B are analyzed by X-ray energy spectrum, and FIG. 7C is obtained. It is found that there is a characteristic peak of selenium near 1.4 KeV, which confirms that nano-selenium is produced by reducing selenite by *Lactiplantibacillus plantarum* KD-2 and is distributed in cytoplasm and extracellular space.

Embodiment 5 Separation, Extraction and Characterization of Nano-Selenium

1. Extraction of Nano-Selenium

Figure 11:
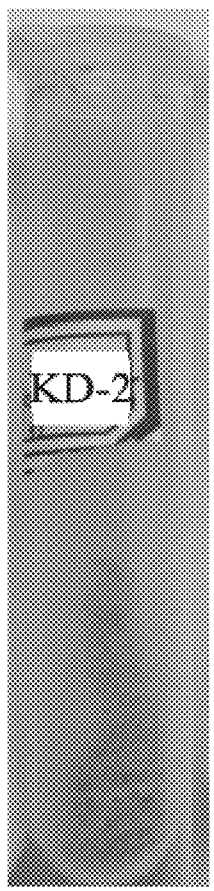
FIG. 11 shows nano-selenium freeze-dried powder transformed by *Lactiplantibacillus plantarum* KD-2.

The culture medium of *Lactiplantibacillus plantarum* KD-2 under the optimum technological conditions is used as raw material, and centrifuged at the rate of 10,000 r/min for 10 min at 4° C. to obtain a precipitate. PBS with pH of 7.0 is added to the precipitate, and 100 μL lysozyme with the concentration of 100 mg/mL is added for standing for 3 h, and then ultrasonic crushing is carried out for 20 min. Tris/HCL (pH 7.0) containing 1% sodium dodecyl sulfate is used for washing, centrifugation at 10,000 r/min for 10 min, and the resulting precipitate is resuspended in sterile water, 1-octanol is added, centrifugation at 20,000 r/min for 5 min, and placed in a refrigerator at 4° C. for 24 h. Then the upper cell debris suspension is discarded, and the bottom nanoselenium precipitate is washed successively with chloroform, anhydrous ethanol, 70% ethanol, and sterile water, and finally pre-frozen for 3 h and then freeze-dried for 30 h to obtain the nanoselenium powder (FIG. 11).

2. Transmission Electron Microscope (TEM) Analysis of Nano-Selenium

Figure 12:
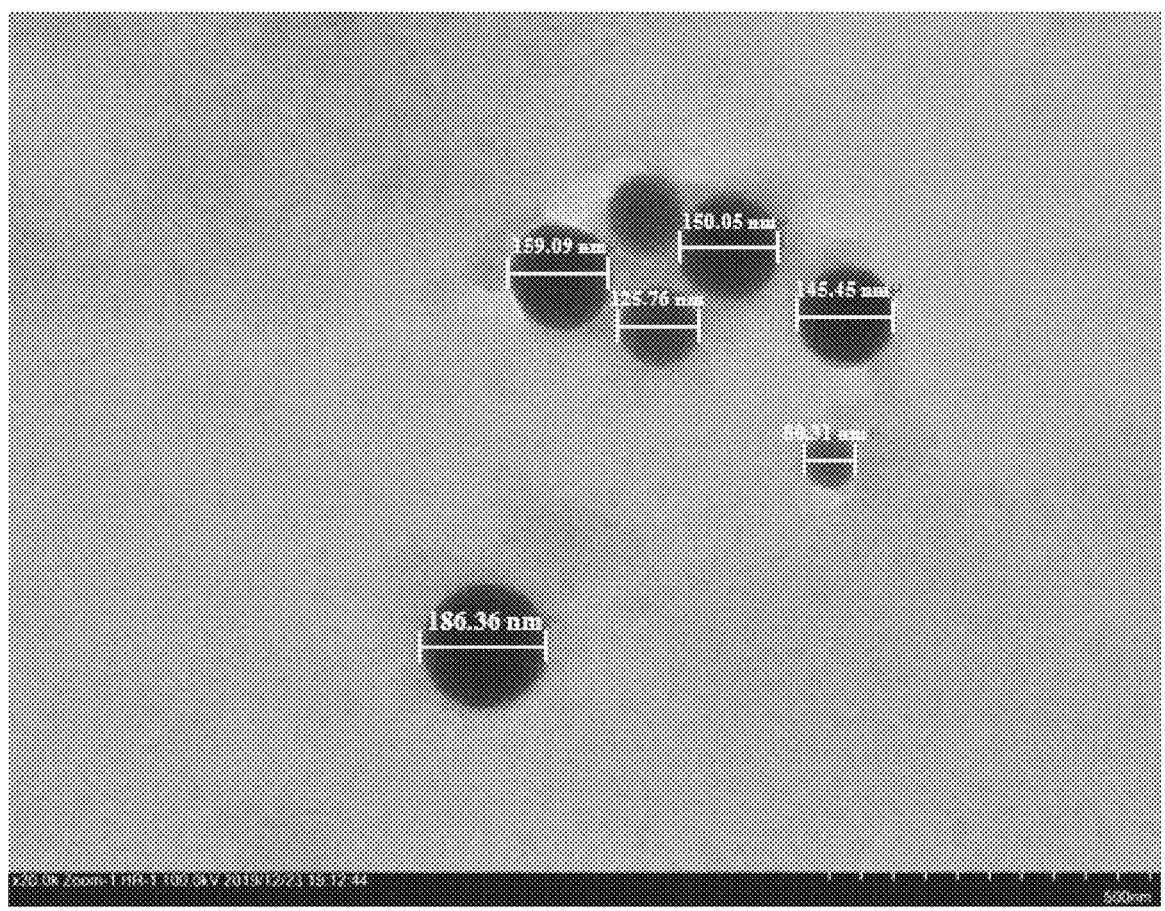
FIG. 12 is a transmission electron microscope (TEM) diagram of nano-selenium.

FIG. 12 is a TEM photograph of nano-selenium prepared by *Lactiplantibacillus plantarum* KD-2. It may be seen from FIG. 12 that the particle size of nano-selenium prepared by *Lactiplantibacillus plantarum* KD-2 is between 80.31-190 nm.

3. X-Ray Photoelectron Spectroscopy (XPS) Analysis of Nano-Selenium

Figure 13A:
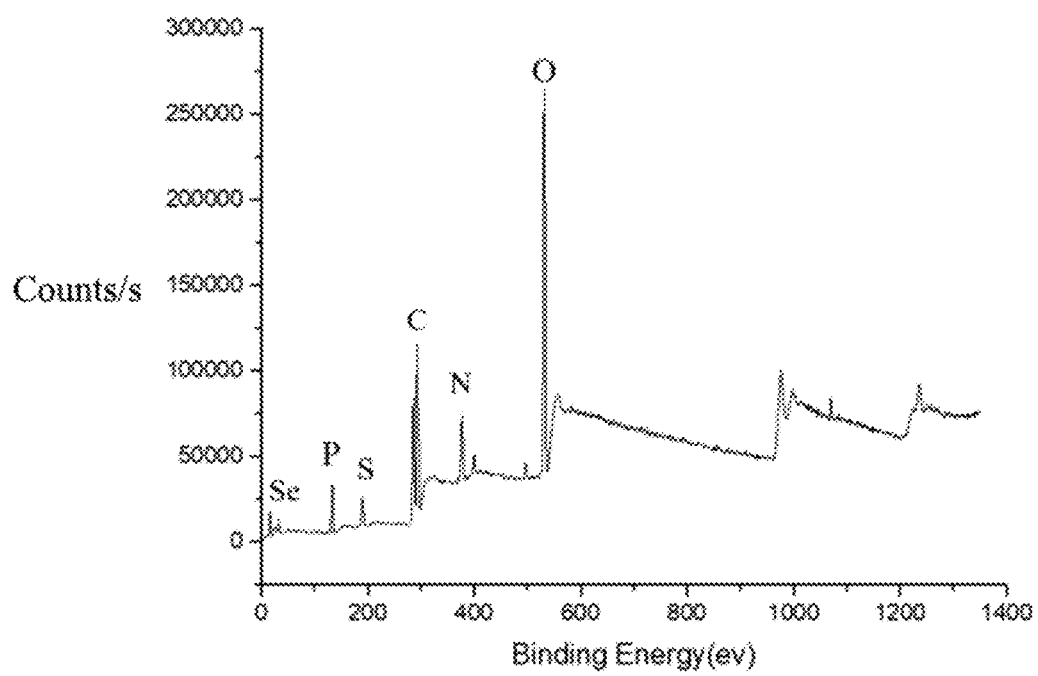
FIG. 13A is the XPS spectrum of nano-selenium prepared by *Lactiplantibacillus plantarum* KD-2.
Figure 13B:
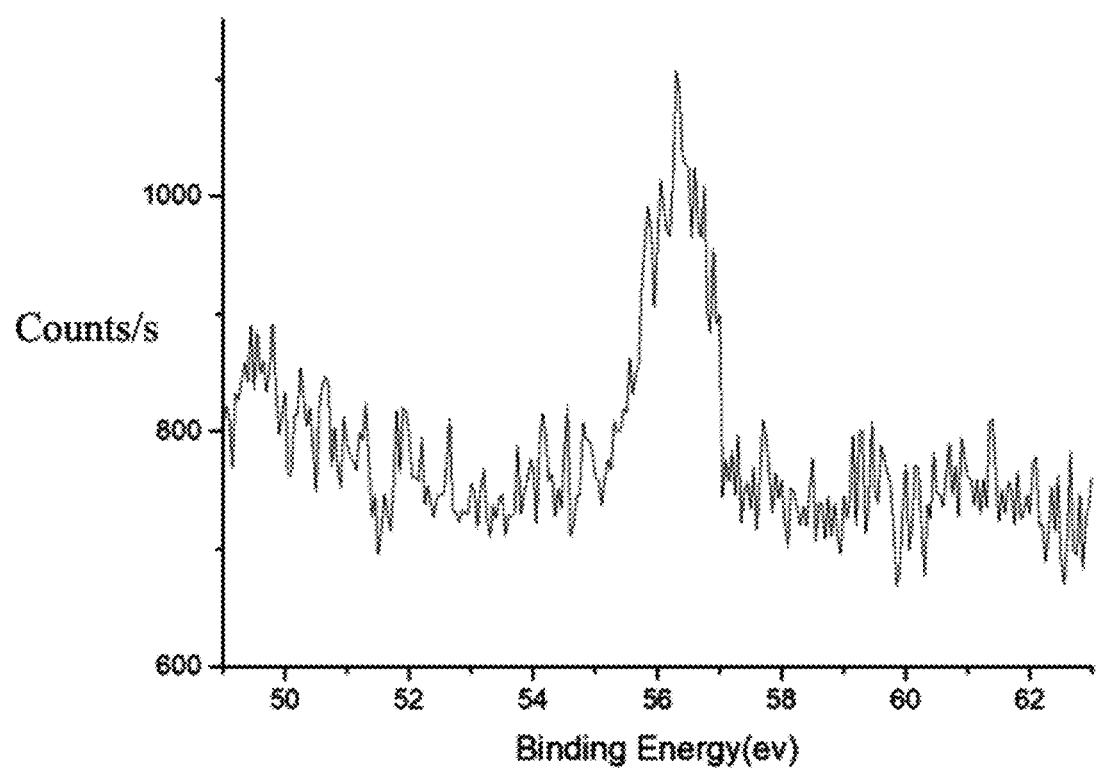
FIG. 13B is the Se3d spectrum of nano-selenium prepared by *Lactiplantibacillus plantarum* KD-2.

The valence States of chemical elements on the surface of nano-selenium transformed by *Lactiplantibacillus plantarum* KD-2 are analyzed by XPS. As may be seen from FIG. 13A, there are elements such as C, O, N, P and S on the surface of nano-selenium, and the intensity of these peaks is stronger than that of selenium, which indicates that there are some biomacromolecules on the surface of nano-selenium, and these biomacromolecules enclose nano-selenium. It may be seen from FIG. 13B that there is a characteristic peak of zero-valent selenium near 55 eV, which proves that zero-valent selenium exists on the surface of nano-selenium.

4. Fourier Infrared Spectrum (FT-IR) Analysis of Nanometer Selenium

Figure 14:
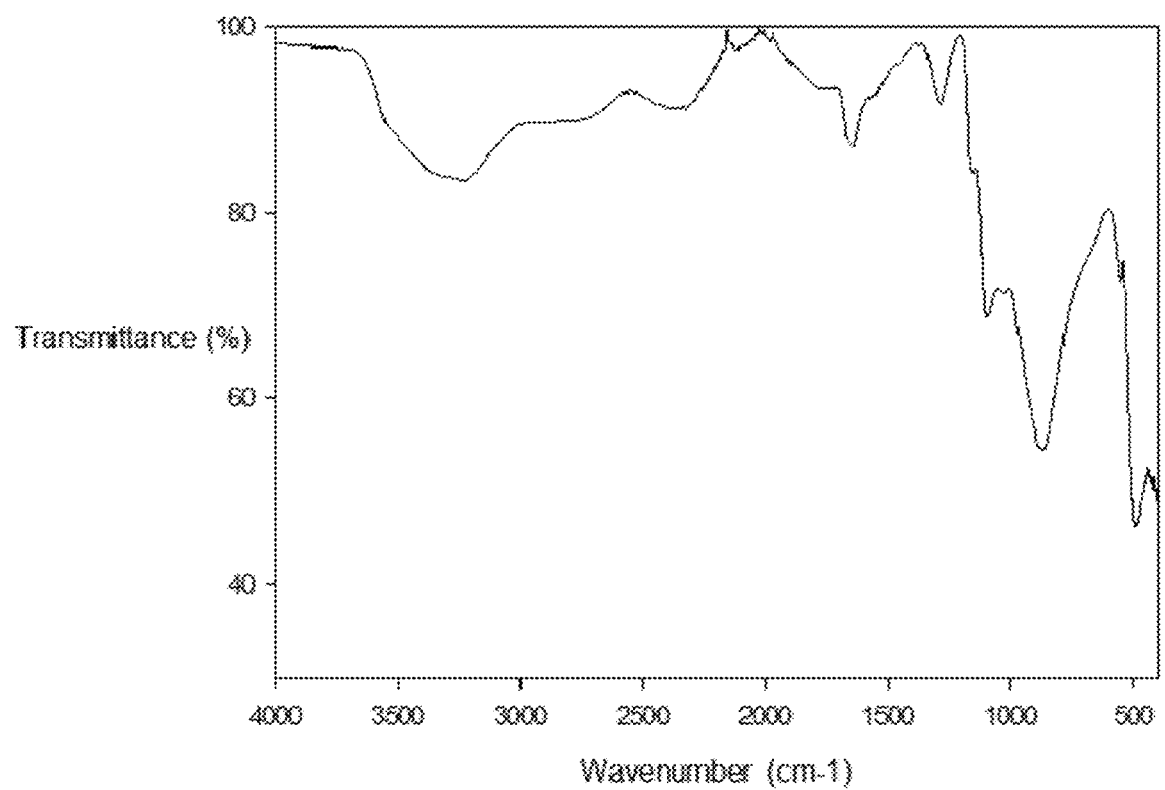
FIG. 14 is the infrared spectrum of nano-selenium prepared by *Lactiplantibacillus plantarum* KD-2.

Fourier infrared spectrum analysis is performed on the nano-selenium powder, where FT-IR spectrum analysis may show the functional groups on the surface of nano-selenium. As may be seen from FIG. 14, the peak at 3233 $cm^{-1}$ corresponds to the stretching vibration of O—H and N—H in the constituent polysaccharides and protein residues. The peaks at 1643 $cm^{-1}$ and 1289 $cm^{-1}$ are amide I band and amide III band of protein, and carboxyl group belonging to amide bond and C—N stretching vibration are typical protein bands. The peak at 1097 $cm^{-1}$ is attributed to the C—O telescopic vibration. These data indicate that nano-selenium synthesized and extracted by *Lactiplantibacillus plantarum* KD-2 may be wrapped by protein and polysaccharide.

Embodiment 6 Selenium-Enriched *Lactiplantibacillus plantarum* KD-2 Fermented Goat Milk According to the ratio of 1:7 (w/v), goat milk powder is mixed with water to make reconstituted goat milk, and then sterilized. The milk is divided into three groups.

The first group is added with 0.05% (w/v) of direct starter TW as control, and the second group is added with 0.05% (w/v) of direct starter TW and sodium selenite (7 μg/mL). In the third group, 0.03% (w/v) of direct starter TW, 0.02% (w/v) of freeze-dried powder of *Lactiplantibacillus plantarum* KD-2 and sodium selenite (7 μg/mL) are added, then cultured at 42° C. for different times (3, 4, 5, 6, 7 h), then refrigerated and cooked for 12 h, and then the pH, acidity, hardness, viscosity, consistency and viscosity index of the obtained probiotic fermented milk are determined and the results are shown in FIG. 15A-FIG. 15C, FIG. 16A-FIG. 16D.

Figure 15A:
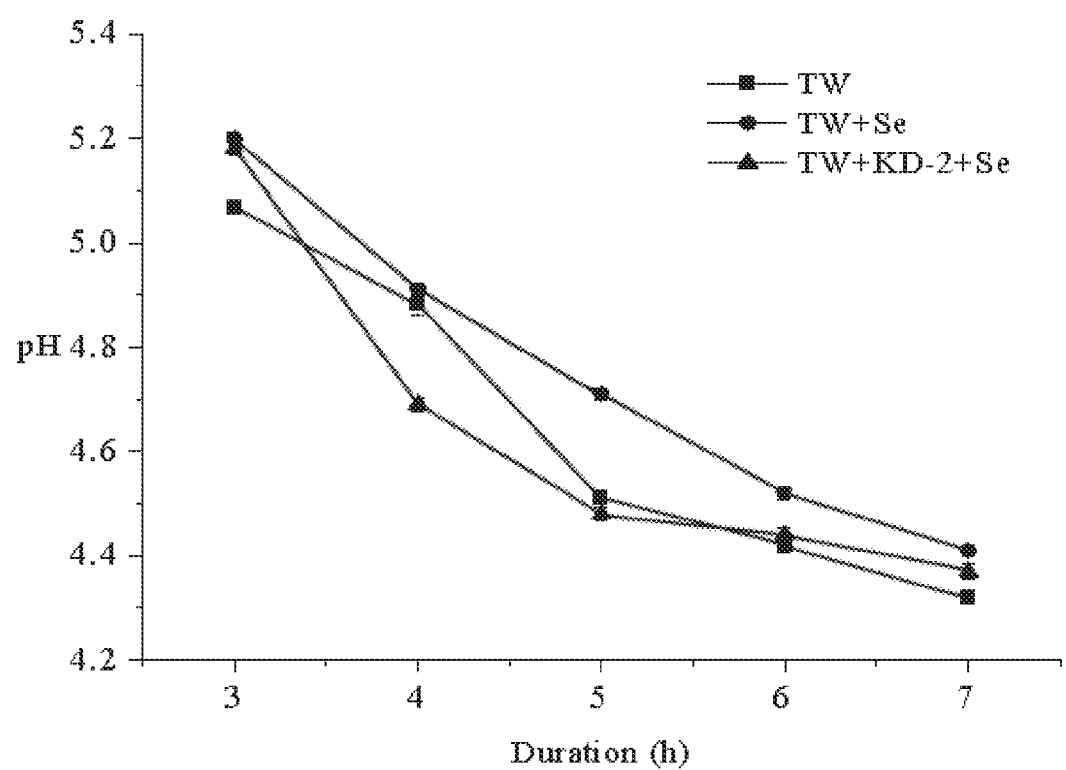
FIG. 15A is effect of fermentation time on pH of fermented goat milk containing nano-selenium.
Figure 15B:
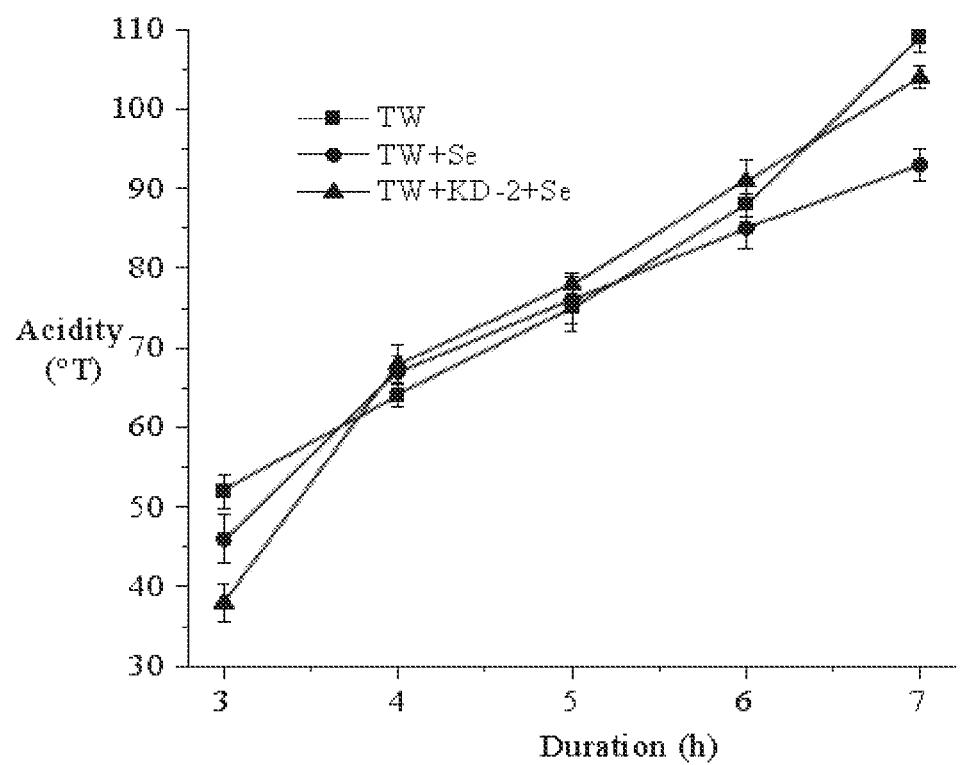
FIG. 15B is effect of fermentation time on the acidity of fermented goat milk containing nano-selenium.
Figure 15C:
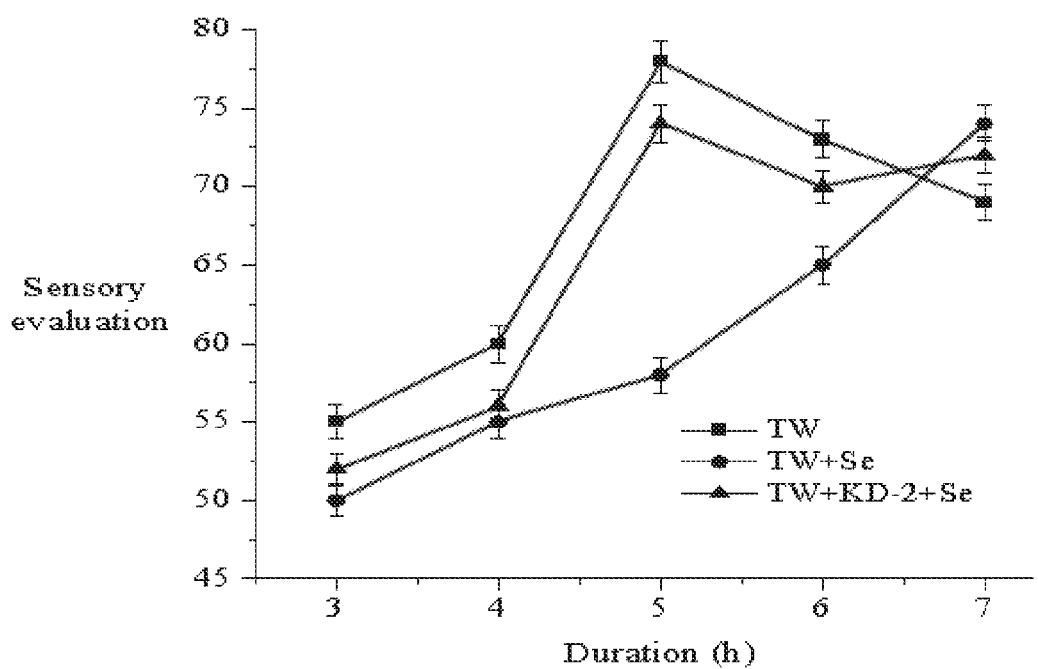
FIG. 15C is effect of fermentation time on sensory evaluation of fermented goat milk containing nano-selenium.
Figure 16A:
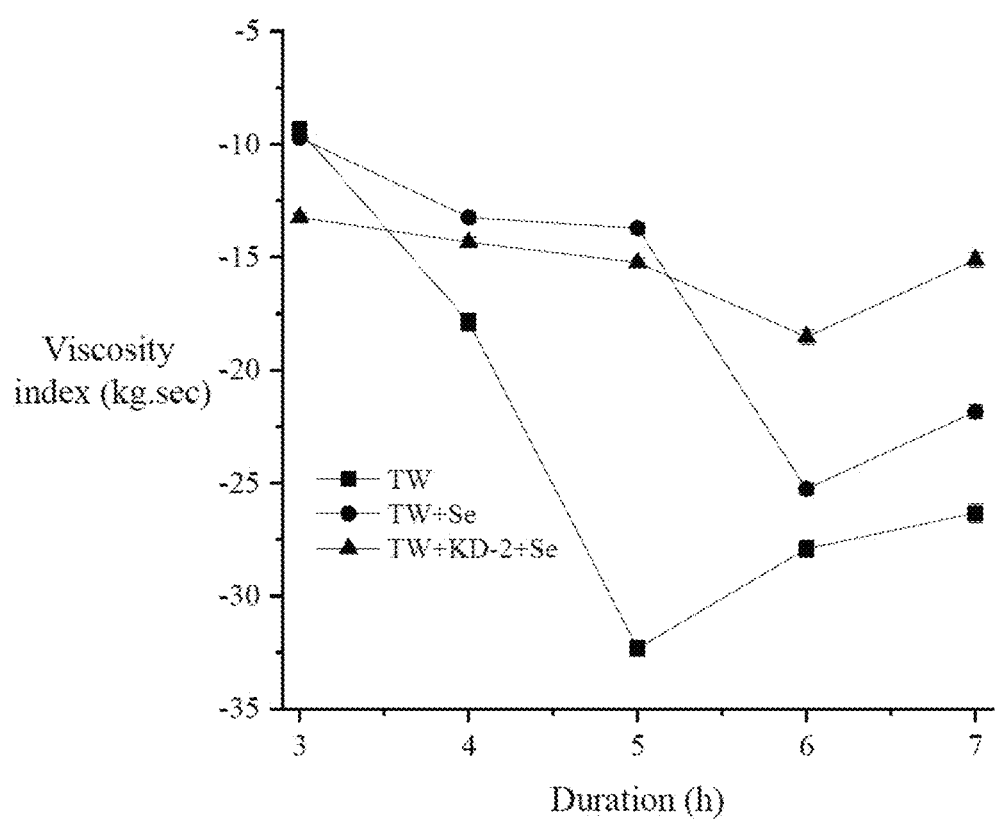
FIG. 16A is effect of fermentation time on the hardness of fermented goat milk containing nano-selenium.
Figure 16B:
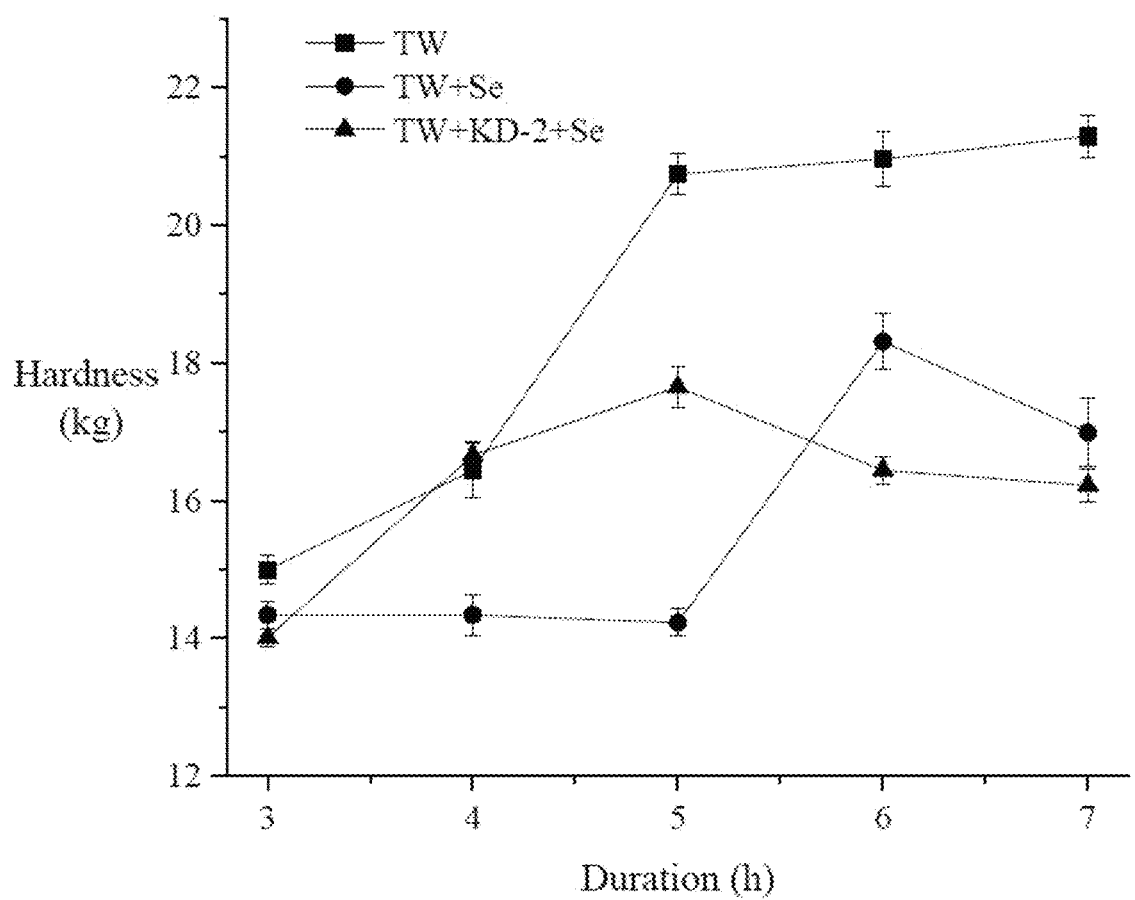
FIG. 16B is effect of fermentation time on the consistency of fermented goat milk containing nano-selenium.
Figure 16C:
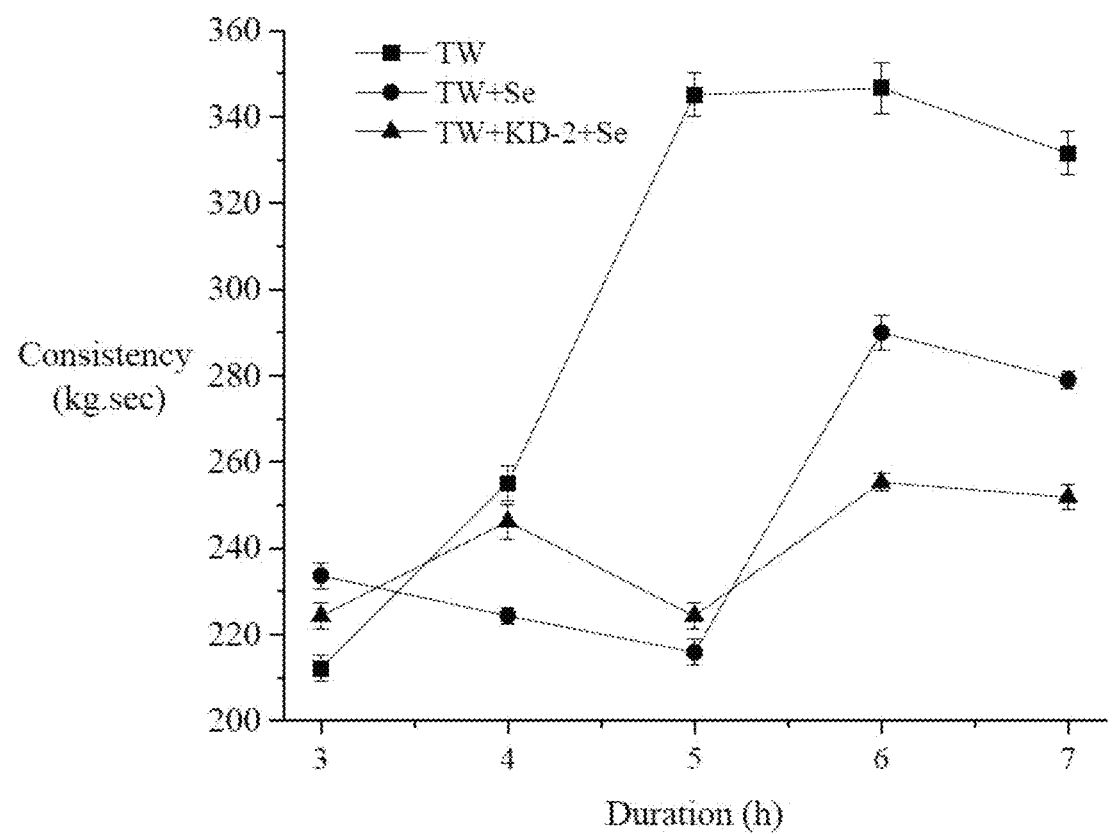
FIG. 16C is effect of fermentation time on the viscosity of fermented goat milk containing nano-selenium.
Figure 16D:
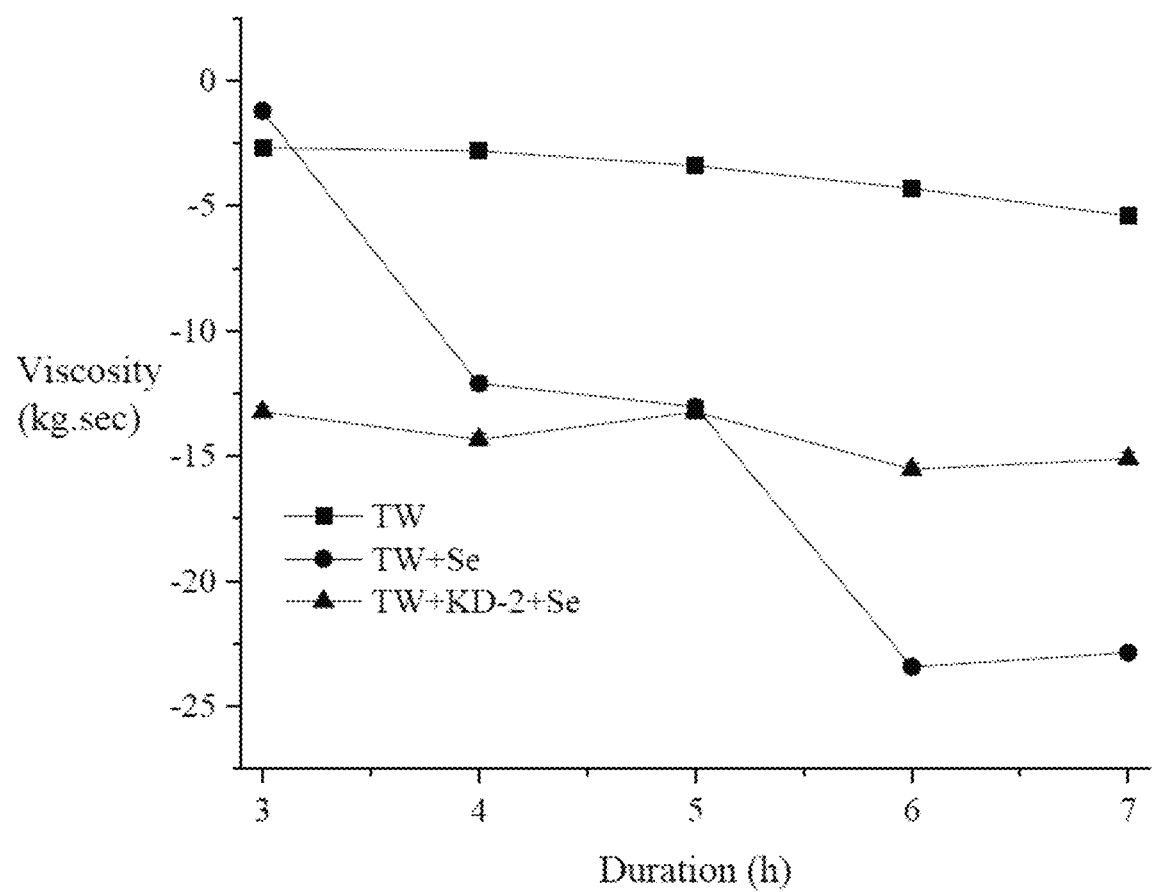
FIG. 16D is effect of fermentation time on viscosity index of fermented goat milk containing nano-selenium.

As shown in FIG. 15A, FIG. 15B and FIG. 15C, the addition of *Lactiplantibacillus plantarum* KD-2 significantly accelerates TW fermentation, with pH below 4.50 for 5 h of fermentation, while the control requires 7 h for pH to reach 4.50.

As illustrated in FIG. 16A-FIG. 16D, the addition of selenium and *Lactiplantibacillus plantarum* KD-2 results in a significant difference in the acid hardness, consistency, viscosity and viscosity index of the fermented goat milk, significantly improving the textural properties of the fermented milk, indicating that it is feasible to develop selenium-enriched *Lactiplantibacillus plantarum* KD-2 fermented goat milk containing selenium-enriched *Lactiplantibacillus plantarum* KD-2 by utilizing the *Lactiplantibacillus plantarum* KD-2.

Embodiment 7 Nano-Selenium *Lactiplantibacillus plantarum* KD-2 Goat Milk Powder Nano-selenium *Lactiplantibacillus plantarum* KD-2 powder prepared in Embodiment 4 is added to goat milk powder by equal increment and dry mixing method according to Table 3 to prepare nano-selenium *Lactiplantibacillus plantarum* KD-2 goat milk powder, the number of viable bacteria is higher than $1.0 \times 10^6$ CFU/g, and the DPPH free radical scavenging rate and ferrous ion chelating rate are higher than 70%.

TABLE 3

Viable count and antioxidant activity of *Lactiplantibacillus plantarum* KD-2 goat milk powder containing nano-selenium

| S/N | Types of milk powder | Nano-selenium *Lactiplantibacillus plantarum* KD-2 added % | Bacterial count CFU/g | DPPH free radical scavenging rate% | Ferrous ion chelating rate % |
| --- | --- | --- | --- | --- | --- |
| 1 | Goat milk powder | 0.03 | $3.55 \times 10^7$ | 71.25 | 71.87 |
| 2 | Goat milk powder | 0.045 | $5.47 \times 10^7$ | 84.62 | 81.28 |

Embodiment 8 Nano-Selenium Goat Milk Powder

Nano-selenium goat milk powder (see Table 4) is prepared by adding the nano-selenium prepared in Embodiment 5 to goat milk at an amount of 15-25 μg per liter, concentrating to a solid content of 45%, and spray drying.

TABLE 4

Oxidation resistance of nano-selenium goat milk powder

| S/N | Types of milk | Nano selenium content μg/L | DPPH free radical scavenging rate % | Ferrous ion chelating rate % |
| --- | --- | --- | --- | --- |
| 1 | Goat milk | 15 | 71.38 | 70.12 |
| 2 | Goat milk | 25 | 88.65 | 84.68 |

Figure 17:
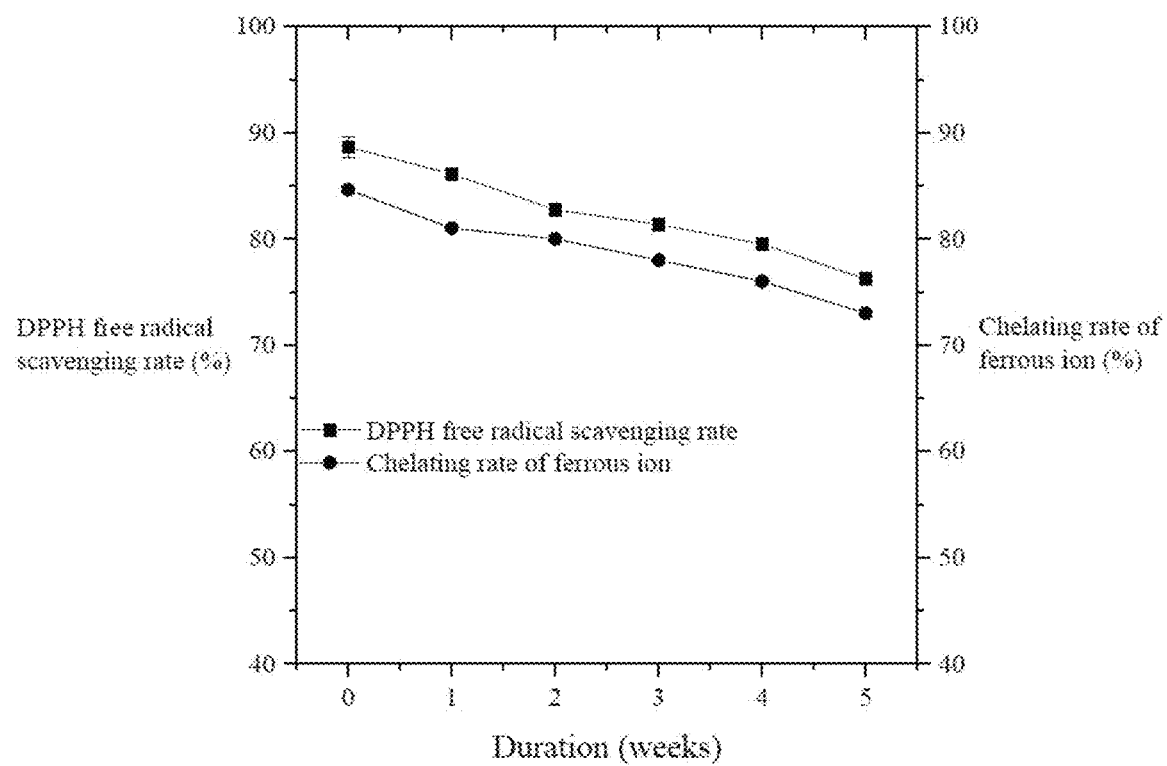
FIG. 17 shows the antioxidant changes of nano-selenium goat milk powder during storage.

The content of nano-selenium in goat milk powder is 120 μg/kg-200 μg/kg, which features antioxidant properties, DPPH free radical scavenging rate is higher than 65%, ferrous ion chelation rate is higher than 65%, and DPPH free radical scavenging rate and ferrous ion chelating ability are still higher than 65% and 60% after 5 weeks of storage, as shown in FIG. 17.

What is claimed is:

1. A strain of *Lactiplantibacillus plantarum* KD-2, wherein the strain is deposited in China Center for Type Culture Collection on Apr. 6, 2023, with a deposit number of CCTCC NO: M2023478.

2. A probiotic goat milk powder, comprising: milk powder and nano-selenium *Lactiplantibacillus plantarum* KD-2 powder, wherein the *Lactiplantibacillus plantarum* KD-2 strain is deposited in China Center for Type Culture Collection under a deposit number of CCTCC NO: M2023478.

* * * * *

SEQUENCE LISTING

```
Sequence total quantity: 1
SEQ ID NO: 1           moltype = DNA   length = 1317
FEATURE                Location/Qualifiers
source                 1..1317
                       mol_type = other DNA
                       organism = synthetic construct
SEQUENCE: 1
gggcggtgtg tacaaggccc gggaacgtat tcaccgcggc atgctgatcc gcgattacta    60
gcgattccga cttcatgtag gcgagttgca gcctacaatc cgaactgaga atggctttaa   120
gagattagct tactctcgcg agttcgcaac tcgttgtacc atccattgta gcacgtgtgt   180
agcccaggtc ataaggggca tgatgatttg acgtcatccc caccttcctc cggtttgtca   240
ccggcagtct caccagagtg cccaacttaa tgctggcaac tgataataag ggttgcgctc   300
gttgcgggac ttaacccaac atctcacgac acgagctgac gacaaccatg caccacctgt   360
atccatgtcc ccgaagggaa cgtctaatct cttagatttg catagtatgt caagacctgg   420
taaggttctt cgcgtagctt cgaattaaac cacatgctcc accgcttgtg cgggccccg    480
tcaattcctt tgagtttcag ccttgcggcc gtactcccca ggcggaatgc ttaatgcgtt   540
agctgcagca ctgaagggcg gaaaccctcc aacacttagc attcatcgtt tacggtatgg   600
actaccaggg tatctaatcc tgtttgctac ccatactttc gagcctcagc gtcagttaca   660
gaccagacag ccgccttcgc cactggtgtt cttccatata tctacgcatt tcaccgctac   720
acatggagtt ccactgtcct cttctgcact caagtttccc agtttccgat gccacttcttc   780
ggttgagccg aaggctttca catcagactt aaaaaaccgc ctgcgctcgc tttacgccca   840
ataaatccgg acaacgcttg ccacctacgt attaccgcgg ctgctggcac gtagttagcc   900
gtggctttct ggttaaatac cgtcaatacc tgaacagtta ctctcagata tgttcttctt   960
taacaacaga gttttacgag ccgaaaccct tcttcactca cgcggcgttg ctccatcaga  1020
ctttcgtcca ttgtggaaga ttccctactg ctgcctcccg taggagtttg ggccgtgtct  1080
cagtcccaat gtgccgatt accctctcag gtcggctacg tatcattgcc atggtgagcc   1140
gttacccac catctagcta atacgccgcg gaccatcca aaagtgatag ccgaagccat   1200
ctttcaagct cggaccatgc ggtccaagtt gttatgcggt attagcatct gtttccaggt   1260
gttatccccc gcttctgggc aggtttccca cgtgttactc accagttcgc cactcac     1317
```